United States Patent
Makower et al.

[19]

[11] Patent Number: 6,090,063
[45] Date of Patent: Jul. 18, 2000

[54] DEVICE, SYSTEM AND METHOD FOR IMPLANTATION OF FILAMENTS AND PARTICLES IN THE BODY

[75] Inventors: Joshua Makower, Los Altos; Claude Vidal; Thomas F. Banks, both of Santa Barbara; Russell J. Redmond, Goleta, all of Calif.

[73] Assignee: C. R. Bard, Inc., Murray Hill, N.J.

[21] Appl. No.: 08/734,638

[22] Filed: Oct. 21, 1996

Related U.S. Application Data

[60] Provisional application No. 60/008,259, Dec. 1, 1995, and provisional application No. 60/016,792, May 7, 1996.

[51] Int. Cl.[7] .................................................. A61F 13/20
[52] U.S. Cl. ................................................ 604/13; 604/15
[58] Field of Search ................................. 606/108, 145, 606/146, 11–15; 604/159, 131, 264, 164, 171, 523, 286, 19, 134–136, 156–158, 21, 48, 57, 59, 93

[56] References Cited

U.S. PATENT DOCUMENTS

| | | | |
|---|---|---|---|
| 654,564 | 7/1900 | Dargatz et al. | |
| 1,061,005 | 5/1913 | Parsegan. | |
| 1,456,828 | 5/1923 | Pistor. | |
| 2,625,934 | 1/1953 | Halliday | 128/303 |
| 3,013,559 | 12/1961 | Thomas | 606/146 |
| 3,062,214 | 11/1962 | Maxwell | 128/330 |
| 3,119,398 | 1/1964 | Bennett et al. | 132/5 |
| 3,467,102 | 9/1969 | Fogarty et al. | 128/348 |
| 3,476,114 | 11/1969 | Shannon et al. | 128/326 |
| 3,589,355 | 6/1971 | Lee | 128/1 |
| 3,638,653 | 2/1972 | Berry | 606/146 |
| 3,699,969 | 10/1972 | Allen | 128/330 |
| 3,713,572 | 1/1973 | Goldsworthy et al. | 226/7 |
| 3,991,766 | 11/1976 | Schmitt et al. | 128/335.5 |
| 3,998,230 | 12/1976 | Miller | 128/330 |
| 4,005,699 | 2/1977 | Bucalo | 128/1.3 |
| 4,084,264 | 4/1978 | Marion | 2/2 |
| 4,197,846 | 4/1980 | Bucalo | 128/218 P |
| 4,258,067 | 3/1981 | Stoll et al. | 426/281 |
| 4,291,013 | 9/1981 | Wahlig et al. | 424/16 |
| 4,347,234 | 8/1982 | Wahlig et al. | 424/15 |
| 4,495,393 | 1/1985 | Janicke | 219/69 M |
| 4,512,800 | 4/1985 | Wirth, Jr. | 75/53 |
| 4,820,267 | 4/1989 | Harman | 604/60 |
| 4,841,968 | 6/1989 | Dunn et al. | 128/335.5 |
| 4,907,590 | 3/1990 | Wang et al. | 606/139 |
| 4,935,027 | 6/1990 | Yoon. | |
| 5,030,232 | 7/1991 | Pham | 623/10 |

(List continued on next page.)

FOREIGN PATENT DOCUMENTS 0 677 297 A1  9/1994  European Pat. Off..
4240533 C1  4/1994  Germany.

OTHER PUBLICATIONS

"A Clinical and Neuropathologic Study of Silk Suture as an Embolic Agent for Brain Arteriovenous Malformaitons," Deveikis, John P., et al., AJNR Am J Neuroradiol 15:263–271, Feb. 1994.

"Controlled release of drugs from surgical suture", Aeseun Loh, Thesis (B.S.)—Massachusetts Institute of Technology, Dept. of Materials Science and Engineering, 1987.

*Primary Examiner*—Wynn Wood Coggins
*Assistant Examiner*—Deborah Blyveis
*Attorney, Agent, or Firm*—Jones & Askew, LLP

[57] ABSTRACT

A method of introducing continuous lengths of filament into the body in surgical procedures in which it is desirable to place a significant amount of material into the body through a small portal. The material so introduced may serve to bulk a tissue or cavity of the body or to occlude a vas, as well as to introduce diagnostic or therapeutic agents into a site in the body. A device for implementing the method has a mechanism for feeding the filament through a conduit in such a manner that sufficient force is applied to the filament that it is forced into the desired site. In one embodiment, a system of reciprocating cannulae and synchronized grippers is used to supply the requisite force to the filament.

13 Claims, 24 Drawing Sheets

U.S. PATENT DOCUMENTS

| | | | |
|---|---|---|---|
| 5,074,840 | 12/1991 | Yoon | 604/15 |
| 5,108,407 | 4/1992 | Geremia et al. | 606/108 |
| 5,121,901 | 6/1992 | Cassidy et al. | 254/134.4 |
| 5,133,731 | 7/1992 | Butler et al. | 606/191 |
| 5,167,624 | 12/1992 | Butler et al. | 604/60 |
| 5,263,927 | 11/1993 | Shlain | 604/13 |
| 5,281,236 | 1/1994 | Bagnato et al. | 606/139 |
| 5,282,829 | 2/1994 | Hermes | 606/219 |
| 5,304,194 | 4/1994 | Chee et al. | 606/191 |
| 5,330,527 | 7/1994 | Montecalvo et al. | 607/152 |
| 5,338,301 | 8/1994 | Diaz | 604/96 |
| 5,346,498 | 9/1994 | Greelis et al. | 606/108 |
| 5,350,385 | 9/1994 | Christy | 606/139 |
| 5,374,261 | 12/1994 | Yoon | 604/385.1 |
| 5,382,260 | 1/1995 | Dormandy, Jr. et al. | 606/151 |
| 5,389,100 | 2/1995 | Bacich et al. | 606/108 |
| 5,514,085 | 5/1996 | Yoon | 604/11 |
| 5,904,648 | 5/1999 | Arndt et al. | 600/120 |

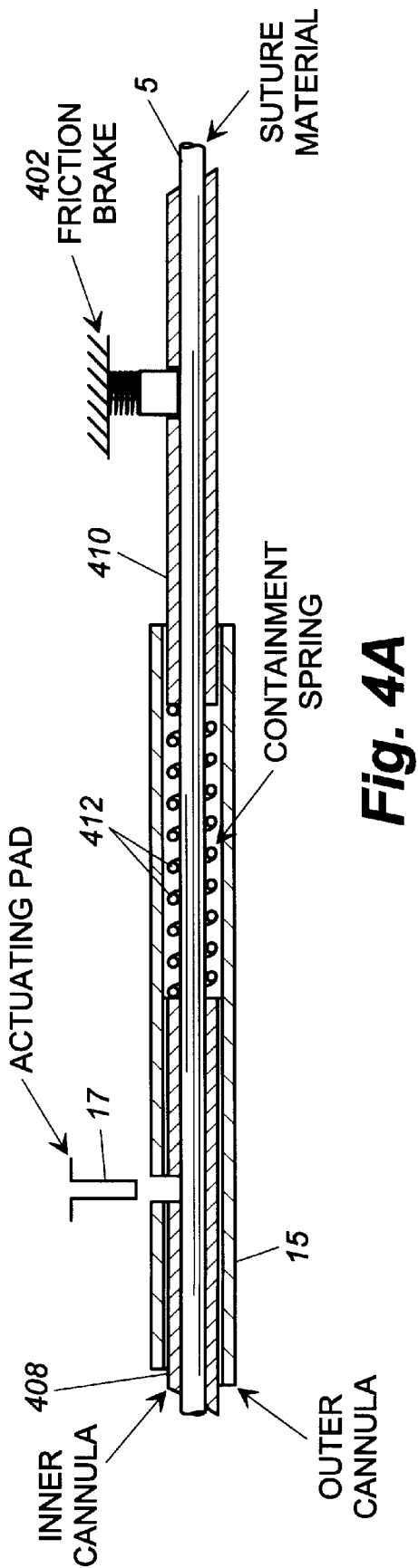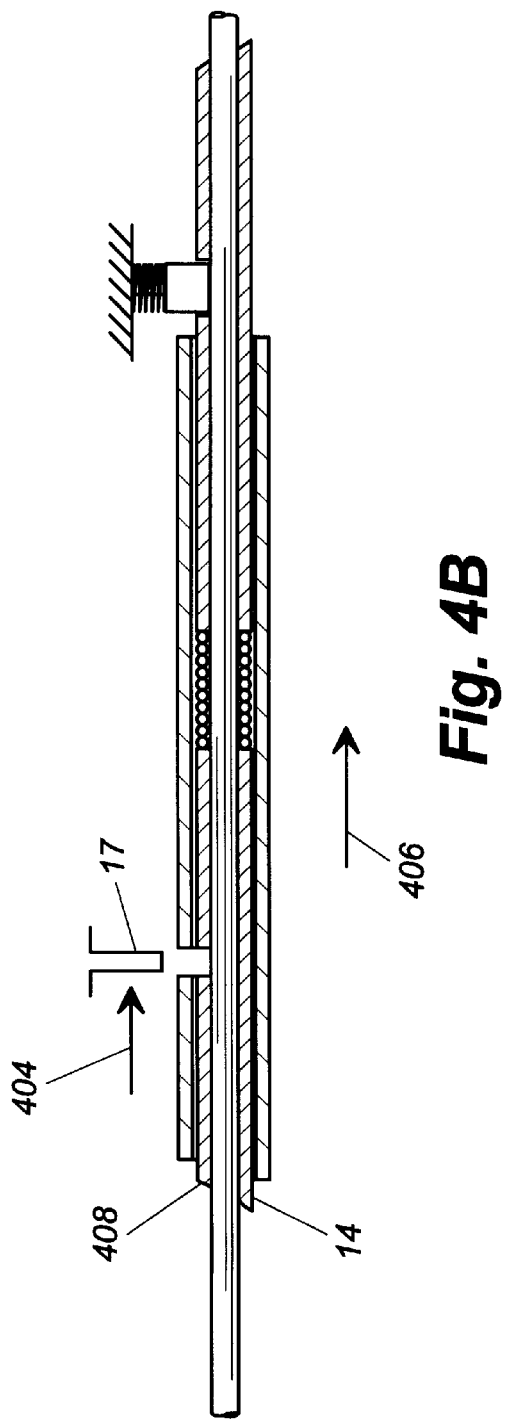

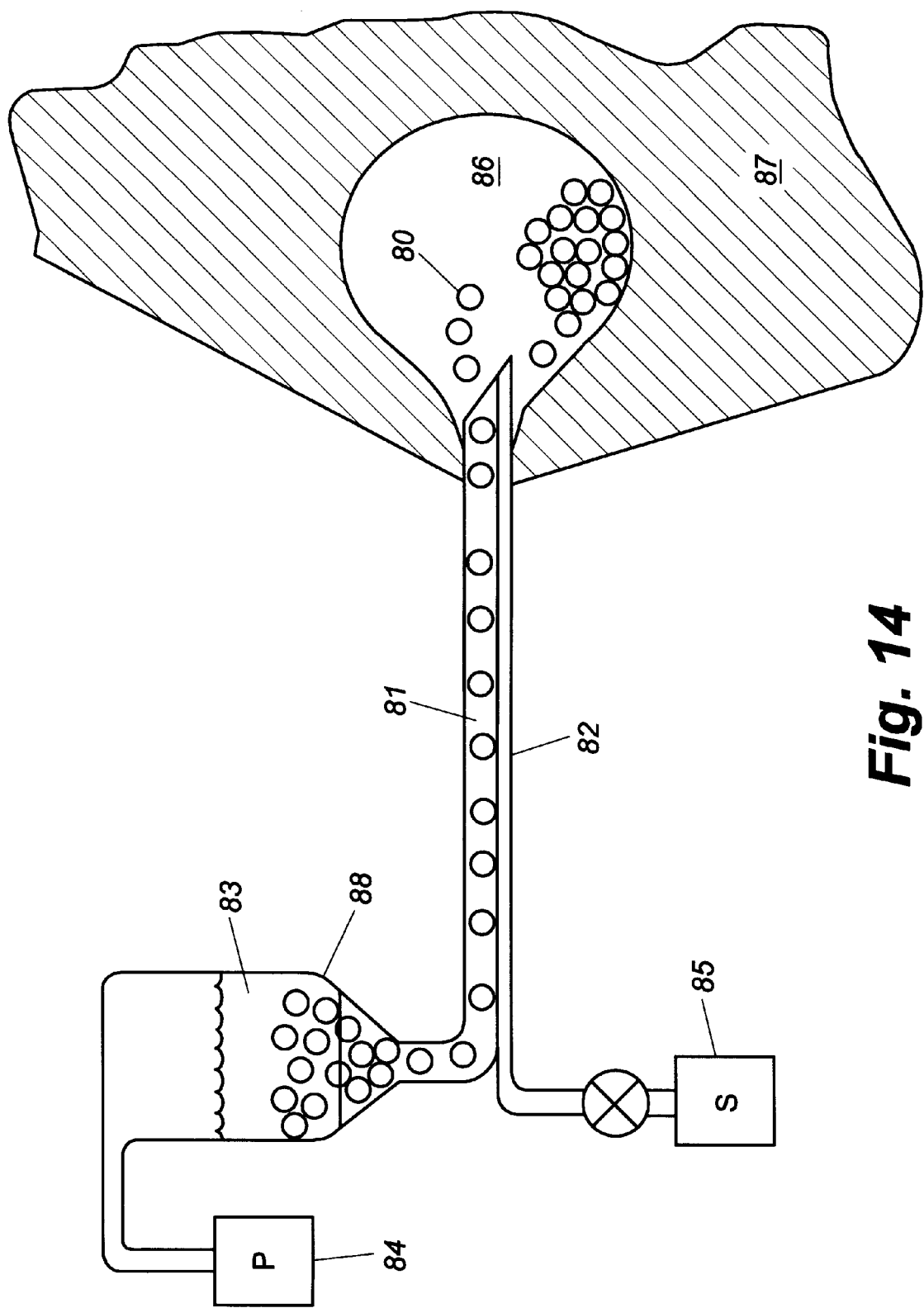

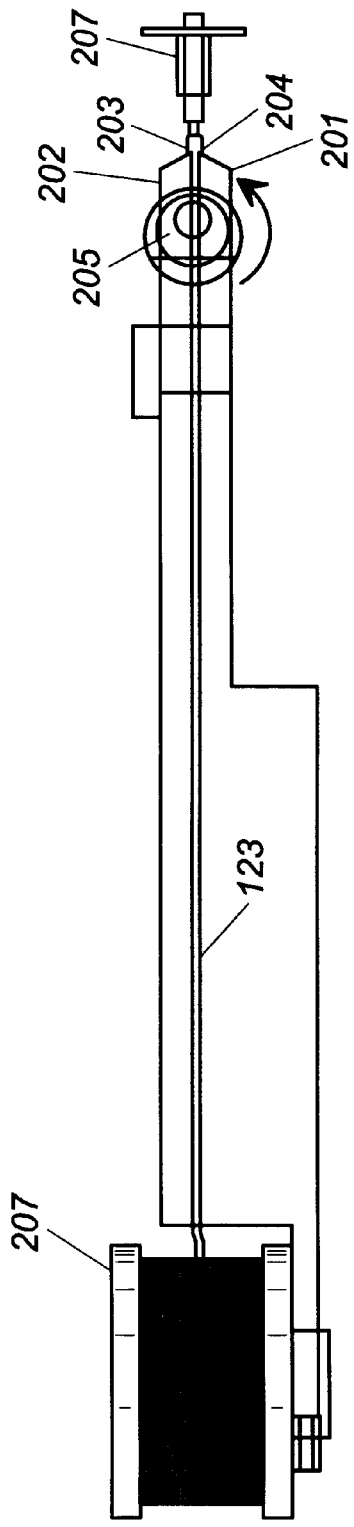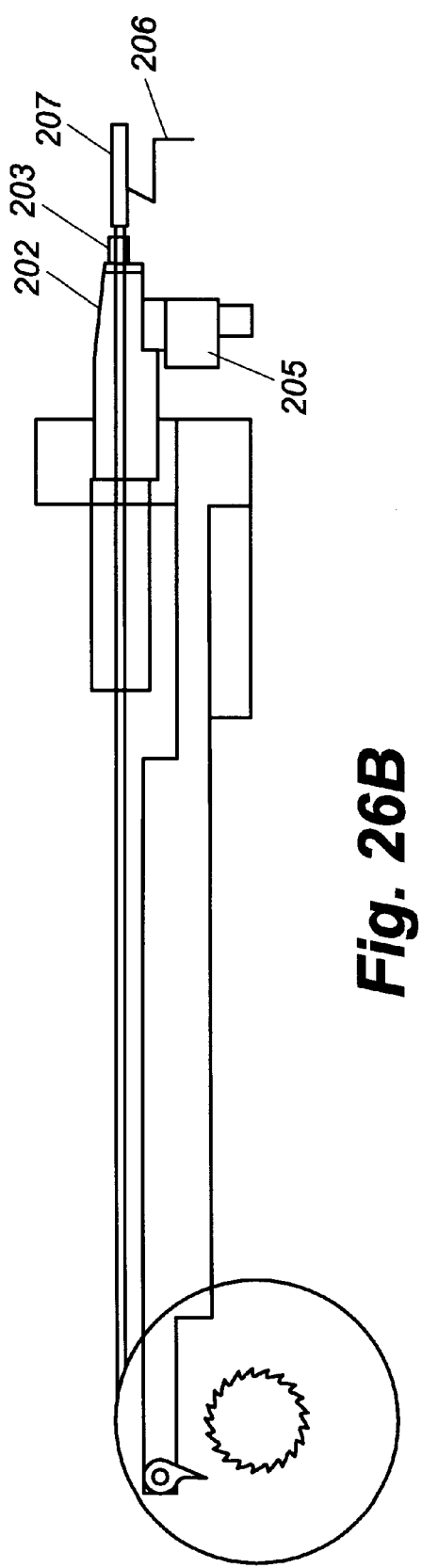
Fig. 26A
Fig. 26B

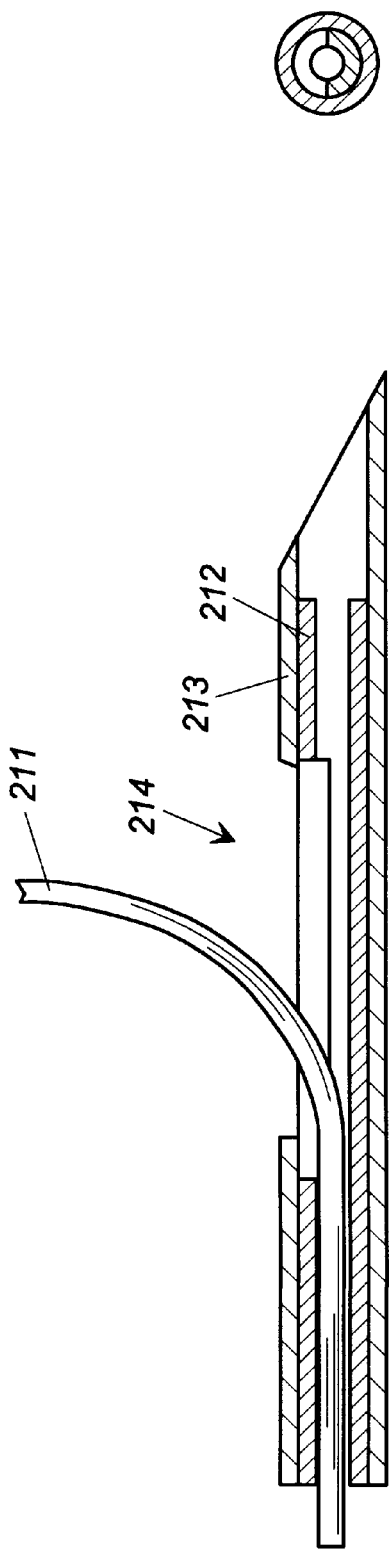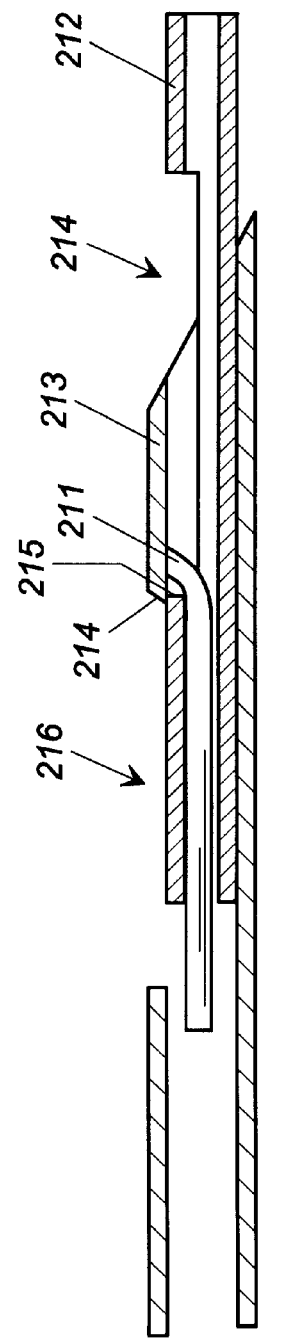

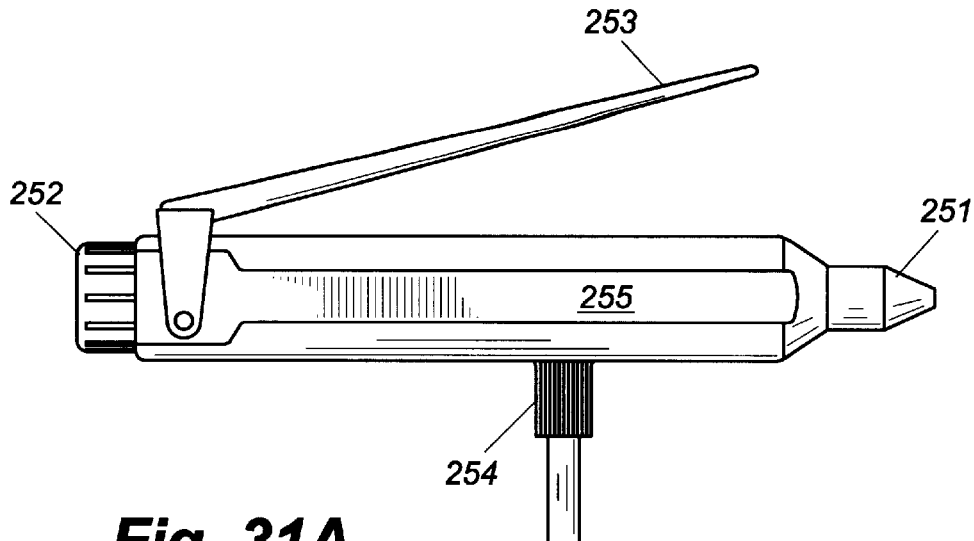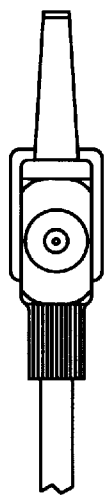
Fig. 31A
Fig. 31B
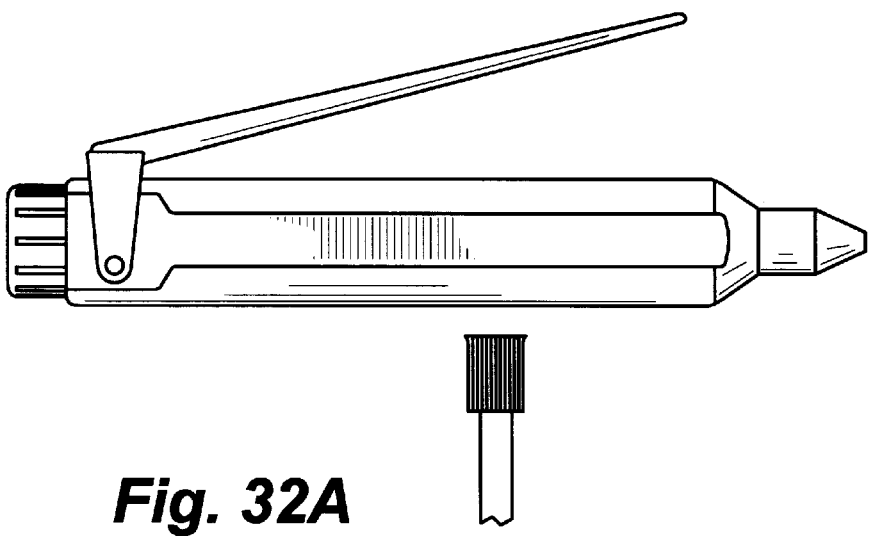
Fig. 32A
Fig. 32B

DEVICE, SYSTEM AND METHOD FOR IMPLANTATION OF FILAMENTS AND PARTICLES IN THE BODY

The present application claims priority from U.S. provisional applications, No. 60/008,259, filed Dec. 1, 1995, and No. 60/016,792, filed May 7, 1996, both of which are incorporated herein by reference.

TECHNICAL FIELD

The present invention relates to a device and method for therapeutic insertion of suture and other materials into body tissue in filamentous and particulate form.

BACKGROUND ART

Increasingly in medicine and surgery, the need arises to place a mass of material either into body tissue or into a space in the body proximate to body tissue for various clinical purposes. These purposes include the bulking of tissue as a therapy for intrinsic sphincteric deficiency (ISD) which gives rise to incontinence. In some types of incontinence, a decrease in urethral resistance leads to urinary leakage during stress. This leakage is embarrassing, and may cause the person to change their life-style to avoid activity. Recently, various injectable materials have been suggested for the purpose of 'bulking' the peri-urethral space, coapting the urethra, and thus increasing the urethral resistance.

Other clinical applications include the implantation of material include the occlusion of aneurysms, arteriovenous malformations (AVMs), and fistulas, as well as the occlusion of the blood supply to tumors, especially cranial tumors, prior to surgery to reduce bleeding during surgery.

To insure that such procedures are minimally invasive, it was clinically determined that bulking, for example, should be accomplished through needle injection. Due to the use of a needle, it was believed that it was necessary to reduce the material to a liquid suspension or particulate so that it might be capable of being passed through a needle into the tissue. This reduced the number of candidate materials significantly. Teflon (PTFE) particles, silicone particles, collagen suspensions, and various other materials were tried. Most of the problems associated with the therapy were associated with the material. For example, collagen resorbed too quickly, creating the need for many repeat therapies. Teflon particles migrate through the body and are thus clinically undesirable.

Known technology has similarly limited the materials which can be delivered transvascularly, endoscopically, or via a conduit in conjunction with a laparoscope. Articles that are delivered by pushing and utilization of these devices are limited, typically, either to fluids or to relatively stiff solids.

The controlled release of drugs from polymer and from surgical suture is another therapeutic modality known in the art. Application of this technique, however, has hitherto required the insertion of suture using conventional methods of pulling the suture into the tissue, as by means of a sewing needle or tweezers, raising difficulties of access to the site of implantation.

SUMMARY OF THE INVENTION

The present invention expands the domain of materials that may be used for bulking as well as for other cellular and drug delivery applications. The invention allows for a filament, as defined below, to be introduced through a needle or other conduit, allowing such well-known biocompatible materials as those used in suture to be considered. With this novel advance, not only can the material have a bulking effect, but depending on the other properties of the filament used, it may add other mechanical attributes such as springiness, rigidity, flexibility, mass, orientation, and permeability. Further, the material being introduced may be a solid, compressed particulate or composite, thereby opening up a range of possible functions the material may perform such as drug delivery, radiation, chemotherapy or thermotherapy. The three-dimensional nature of the end result may be very appropriate to provide a scaffolding for cellular ingrowth for cells either injected with the filament, or those induced to grow into the matrix.

The device is capable of placing a significant amount of material in the body through a small portal, i.e., an opening in the body as defined below. This material may preloaded with a drug, or cells, or some other active material to produce some desired effect with the body. The dosage may be controlled by the length of the filament and the nature of the preloading, and may be modified at the time of delivery to the length of choice. Such a method may be useful for the delivery of subcutaneous heparin, insulin, contraceptive substances, and other pharmaceuticals useful for heart disease, smoking cessation, etc. The advantage of this approach over other subcutaneous drug delivery devices is its extremely low profile, and the ease in which it is positioned within any site in the body, in particular, in the proximity of the tissue to be affected.

In accordance with a preferred embodiment of the invention, a method is provided for modifying a tissue property of a subject, wherein the method consists of providing a quantity of filament, opening a portal in the body of the subject, where both "filament" and "portal" are defined below, inserting the filament through the portal into a region in the vicinity of the tissue, and localizing the filament in the region so as to modify the tissue property. The tissue property to be modified may include the mass, bulk, orientation, rigidity, flexibility, springiness, and permeability of the tissue. The filament is inserted directly, or with the aid of an endoscope or a laparoscope. Embodiments of the invention provide methods for bulking the tissue of a subject, coapting the walls of a vas, where "vas" is defined below, occluding a vas, preventing pregnancy, sterilizing a subject, clotting an ulcer, treating an aortic aneurism, treating a bleeding esophageal varix, providing chemotherapy, releasing a drug, catalyzing biochemical reactions, providing birth control, supporting cell growth in a subject, sewing body tissue, delivering anesthesia, and delivering a stent into a vas. Each of the aforesaid methods has the steps of providing a quantity of filament and inserting it into the body. The filament may be preloaded as described above. In further embodiments of the invention, a continuous length of filament may be severed to provide a desired length of filament within the body of the subject, and fluid may also be injected into the subject in conjunction with the filament. Additionally, in accordance with an alternate embodiment of the invention, suture is provided in particulate form, suspended in a liquid carrier to create a suture suspension, and inserted through a portal in the body of a subject to modify a tissue property that includes at least one of the mass, bulk, orientation, rigidity, flexibility, springiness, and permeability of the tissue.

In another embodiment of the invention, a method is provided for removing filament from a site in the body that consists of the steps of inserting a hollow shaft into the site, hooking the filament with a hooked tool, and withdrawing the filament via the hollow shaft.

In accordance with another aspect of the invention, a device is provided that has a conduit for insertion into a designated site in the body, and a feeding mechanism for supplying filament along the axis of the conduit in a manner such that support is provided across all lengths of the filament longer than three times the diameter of the filament. The conduit may be rigid, as well as semi-rigid or flexible.

In one embodiment of the invention, the feeding mechanism has an inner cannula with an inner diameter corresponding generally to the diameter of the filament and a mounting arrangement, which may be a coaxial outer cannula, for permitting the axial movement of the inner cannula. Finally, an actuator mechanism is provided for urging the inner cannula in axial reciprocation consisting of forward motion and retrograde motion with respect to the mounting arrangement. In alternate embodiments, the actuator mechanism may have a combination of grippers or a gripper and a brake. Additionally, the inner cannula may have distinct proximal and distal segments and a containment spring for retracting the distal segment toward the proximal segment during retrograde motion of the distal segment.

In further embodiments of the present invention, a tip may be provided on the mounting arrangement for penetrating body tissue, and a window may be provided proximally to the tip to allow filament to be fed into the site. Filament cutters are provided in several alternate embodiments to allow desired lengths of filament to be left in the body. In one filament cutter embodiment, a torquable head is disposed adjacent to the distal end of the conduit with a shearing surface disposed on at least one of the torquable head and the distal end of the conduit such that rotation of the torquable head severs the filament. In another filament cutter embodiment, a shearing surface is provided on at least one of the inner cannula and mounting arrangement of the device such that relative motion of the inner cannula and mounting arrangement cause shearing of the filament.

Other filament feeding mechanisms are provided in alternate embodiments of the invention which include conveyor belts engaged against the filament, a toothed wheel and idler wheel for advancing the filament, and a reciprocating shaft which drives the filament forward in the shaft and then springs back in disengagement from the filament. A motor may be employed for repetitively cycling the feeding mechanism.

In accordance with another aspect of the present invention, a device is provided for removing a filament from a site in the body where the device consists of a conduit and a hook for snagging and withdrawing the filament through the conduit.

BRIEF DESCRIPTION OF THE DRAWINGS

FIGS. 4A and 4B show cross-sectional views of a filament feeding mechanism in a the reset stage of a filament feeding cycle in accordance with the embodiment of the invention shown in FIG. 2.

FIG. 14 illustrates the mechanism through which particle may be injected into the body in accordance with another embodiment of the invention.

FIGS. 18 through 26 illustrate various embodiments of the invention for achieving the movement of a filament along a desired path so as to permit implantation of the filament;

FIG. 19 illustrates an embodiment for achieving movement of a filament utilizing a toothed drive wheel against which the filament is engaged by an idler wheel;

FIG. 20 illustrates an embodiment, similar to that of FIG. 19, utilizing a toothed drive wheel against which the filament is engaged by an idler wheel, but wherein the filament is also engaged against the drive wheel by a guide having an arcuate surface that general conforms to the radius of the drive wheel;

FIG. 22 illustrates an embodiment for achieving movement of a filament utilizing a toothed drive wheel against which the filament is engaged by a tubular guide;

FIGS. 26A and 26B illustrate an embodiment for achieving movement of a filament utilizing a pair of arms that are caused to reciprocate axially while being alternately opened and closed at the opposite ends of each stroke;

FIGS. 27A through 31D illustrate embodiments of the invention in which a region proximate to a tip of a cannula carrying a filament is provided with an arrangement, for cutting the filament, utilizing a concentrically disposed member and a window in both members through which the filament is placed and severed;

FIGS. 27A and 27B illustrate an embodiment wherein the outer member is pulled proximally with respect to the inner member to achieve cutting;

FIGS. 31A and 31B, and 32A and 32B, illustrate a possible configuration for a case for an embodiment similar to that of FIGS. 26A and 26B.

DETAILED DESCRIPTION OF SPECIFIC EMBODIMENTS

Figure 1:
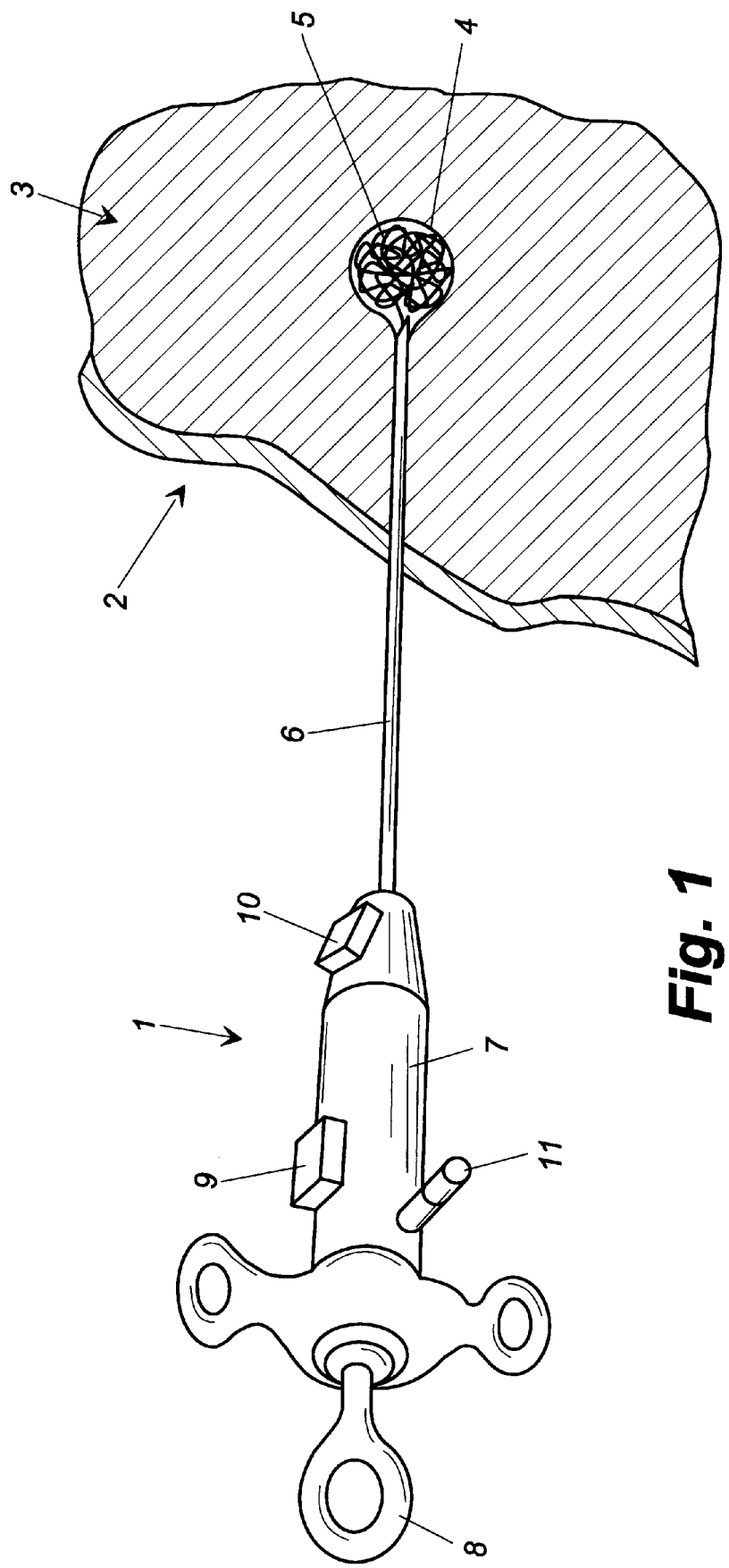
FIG. 1 is a schematic illustration of a filament injection device 1 in accordance with a preferred embodiment of the present invention.

In order to provide an overall understanding of the present invention, the method, system, and device of the invention will be discussed with reference to the application of the invention to provide tissue bulking. However, it will be understood by persons of ordinary skill in the art that the general method, system, and device, described herein, are equally applicable to all cases in which filament injection would have value. A list of possible uses for the technology includes, but is not limited to, the injection of a filament-based system of drug delivery into tissue, the subcutaneous or interstitial injection of a filament for the purpose of bulking, shaping, applying pressure, or adding other mechanical properties (such as springiness or rigidity), and the injection of a filament to act as a matrix or lattice in which a cellular process may proceed (i.e. bone replacement, healing, implanted cellular scaffolding).

Other clinical uses include the injection into the body of a filament bearing other properties such as radiopacity, magnetism, radioactivity—radiation, or fluorescence, all suited for application as a clinical tracer or therapeutic agent.

Similarly, the filament may have chemical properties which allow it to serve as a tracer of specified biochemical processes or as a catalyst to stimulate or enhance desired reactions within the tissue. This invention represents a new concept in the delivery and retrieval of mass as well as of therapeutic and diagnostic agents.

The applications of tissue bulking alone are manifold, once it is appreciated that tissue bulking may be achieved conveniently and at low risk using the method, system, and device of the present invention. Tissue bulking applications include, but are not limited to periurethral bulking of the urinary sphincter, support of the urethra, therapy of vesicourethral reflux, prevention of esophagal reflux via the gastroesophageal sphincter, and treatment of the anal sphincter for treatment of fecal incontinence. Other applications of tissue bulking which may be achieved using the present invention include the bulking of blood vessels, both internally or externally, in association with the treatment of bleeding ulcers. The applications listed are given by way of example, though it is to be understood that the scope of the invention is not limited to the applications listed but includes all applications wherein filamentous material is usefully injected into the body.

As used in this specification and in the claims hereto appended, a material, provided in a threadlike form, will be referred to as "flaccid" if its buckling stress, measured in units of force per unit cross-sectional area of the material, is less than or comparable to the shear strength that is typical of soft body tissue (such as the dermis). Shear strength is expressed in the same units as stress. Buckling stress, as is known in the mechanical arts, refers to the force per unit area applied axially to a member which causes deformation of the member in a direction orthogonal to the axis of the member. It is also known in the mechanical arts that the buckling stress of a member is proportional to the off-diagonal compressive modulus, (i.e., the ratio of axial compressive stress to the strain induced transverse to the axial direction) and inversely proportional to the square of the ratio of unsupported length to diameter of the member. Thus, the longer or finer a thread is, the less force per unit area is required to cause it to buckle.

Clearly, it is known that rigid, needle-shaped implements, such as all manner of needles or staples, may be driven into tissue upon application of sufficient axial force along the direction of insertion. By way of contrast, the present invention teaches a method of inserting materials which are flaccid rather than rigid. In view of the definition of "flaccid" provided above, flaccid materials are inherently incapable of being driven into tissue by the application of axial force. These materials are referred to, collectively, as "filament." More particularly, as used in this specification and in the claims hereto appended, the term "filament" refers to a flaccid material, and may include biocompatible materials such as polypropylene, Nylon, DACRON™, polybutylester, polybutylethylene, polyglycolic acid (PGA), and variations thereof, and any other material, naturally occurring, biological, or man-made, which has been chosen for a particular application on the basis of biocompatibility, biodegradability, or any other desirable property. Other filament materials useful in particular clinical applications are composite, woven, or solid, and include silk, metal, 'gut', collagen, elastin, cartilage and bone. The term "filament" encompasses, particularly, all materials, such as polypropylene, currently supplied and used as suture material and referred to thereas. Additionally, the term "filament" encompasses the use of materials having shape memory, such as nitinol, which may be used to particular clinical advantage. Whereas many of the foregoing materials may be formed into a wire-shaped member that is not flaccid as defined herein, the term "filament" in this description and the accompanying claims is limited to the embodiment of such materials in their flaccid forms.

Since the "filament" is flaccid, it will be appreciated that materials of this category, if pressed, unguided, against the surface of body tissue, are likely to buckle rather than to cleave the surface, penetrate into the body tissue, or expand or dissect a space into the tissue.

When a filament is bent, such as under its own weight or due to compressive buckling, the inner regions yield under compression. Force applied to the distal end of a bent filament by driving it against a surface is no longer truly axial and has a vector component which leads to further bending. Plastic deformation may inhibit the return of the filament to the original configuration even after removal of the load. However, the filament need not undergo any plastic deformation if it is suitably introduced and trapped within the body tissue, in accordance with the present invention.

In the prior art, suture is treated as a flaccid material in that it is pulled through tissue, as by a needle or tweezers, rather than pushed. For suture or other filament sufficiently fine, large forces per unit cross-sectional area can be developed, using the teachings of the present patent, over small cross sectional areas. The force per unit area applied by the tip of the filament can readily exceed the shear strength of the body tissue so that the filament can thereby cleave and penetrate the tissue. The recognition of this ability of a filament, using the methods of this invention, to penetrate body tissue, enables the host of clinical applications which are described herein.

As used in this description and in the appended claims, a "portal" for insertion of filament into the body refers to any naturally existing or created opening into the body or a tissue. The invention teaches the insertion of filament into the vicinity of a tissue, where, as used in this description and in the appended claims, a "vicinity" includes at least a portion of the tissue itself, as well as its walls, and proximate tissue or body cavity. Since some tissues may be too small, fragile, or sensitive to permit direct insertion of filament, filament may be inserted, in accordance with the teachings of the present invention, into proximate tissue that is near but not directly associated with the target tissue.

Additionally, insertion of filament may be achieved via a vas, where, as used in this description and in the appended claims, the term "vas" refers to any duct, vessel, passageway or cavity occurring in the body, either by natural anatomical formation or through surgical intervention.

FIG. 1 illustrates a filament injection device 1 in accordance with a preferred embodiment of the present invention. Here a needle 6 is inserted through the skin 2 into the body 3. A small filament 5 is injected into an interstitial space 4. The needle 6 is attached to a housing 7 which has an inlet 11 for fluid, a fluid control 8 for fluid injection, an injection control 9 to advance the filament, and a cut control 10. Those skilled in the art will recognize that needle 6 may also be a rigid, flexible, deformable, malleable, semi-rigid or semi-flexible cannula or catheter inserted percutaneously, endoscopically or transvascularly. Further, filament 5 may also be a resorbable or non-resorbable suture, wire, or any of the other materials comprised within the definition of "filament" given above. This filament may be a composite material embedded with drugs, cells, or radioactive substances. The combination of drugs with polymer to provide programmed release of the drugs within the body is known, as described in A. Loh, *Controlled Release of Drugs from Surgical Suture*, 1987, which is herein incorporated by reference. The insertion into the body of a filament which has been preloaded with a therapeutic or diagnostic agent, whether by techniques of embedding or impregnating within the filament material or otherwise bonding to the filament, whether at the time of manufacture or at the time of insertion into the body, is included within the scope of the invention. While no other working channels are shown in the device, those skilled in the art will recognize that the modification of the device to permit additional instrumentation to be passed within or along-side the device does not depart from the invention. Such other channels may be provided for introducing energy guides, wires, endoscopic visualization devices or surgical tools. The device as shown would be easily advanced into the periurethral space for tissue bulking or drug delivery to treat incontinence, or the perivascular space for venous reconstitution or drug delivery, or the interstitial space within a tumor for chemotherapy, radiation or magnetic thermal therapy.

In this specification and in the appended claims, the term "distal" denotes the end of the filament injection device 1, or the end of any of the component parts of filament injection device 1 such as conduit 6, which is located toward the point of delivery of filament 5 into the body 3. Conduit 6 serves as the delivery cannula through which filament 5 is introduced into the body of the subject. Similarly, in this specification and in the appended claims, the term "proximal" denotes the end of the filament injection device 1 or the end of any of the component parts of filament injection device 1 which is located away from the point of delivery of filament 5 into the body 3. Because of the need to minimize the diameter of distal end 12 of filament injection device 1, in order to avoid leaving a large hole in the body 3 of the subject, the bulkier suture feeding mechanism typically resides in the bulkier proximal section 7 of the device. Therefore, the feeding mechanism, described below, cannot pull on the filament but must push it forward. In order to allow for pushing a flaccid material into the body, the zone between feeding mechanism 7 and conduit 6 over which filament 5 is unsupported must be kept to a minimum. In some preferred embodiments of the invention, there is no unsupported length of filament 5, while, in other embodiments, a length of filament 5 is unsupported, and is, typically, no larger than three times the characteristic diameter of the filament.

Figure 2:
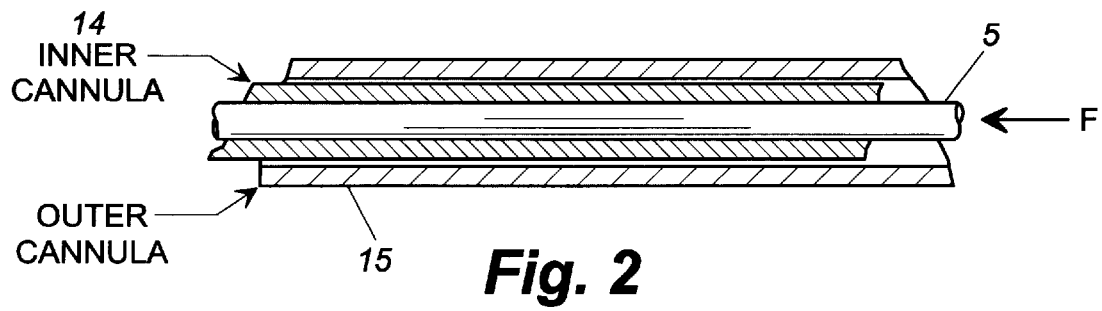
FIG. 2 illustrates the principal components of a filament injection device in accordance with a preferred embodiment of the present invention.

Referring now to FIG. 2, wherein the principal components of a filament feeding device used, in accordance with a preferred embodiment of the invention, to advance the filament into the tissue. Inner cannula 14 is a tubular section having a diameter closely matched to the diameter of filament 5 for which inner cannula 14 provides support. Inner cannula 14 prevents filament 5 from buckling or jamming as a result of the axial force pushing it into the body, and is, in turn, retained axially within a coaxial outer cannula 15. In alternate embodiments, inner cannula 14 may be retained by other manner of mounting arrangements, to include channels, as is well known to a person of ordinary skill in the art.

Figure 3A:
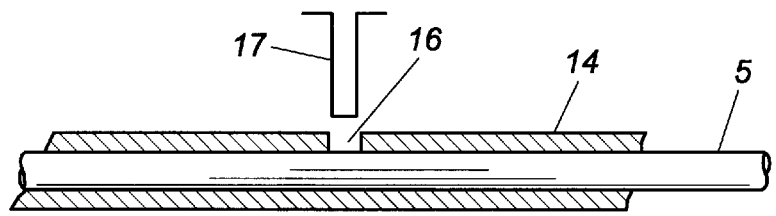
FIGS. 3A–3C show cross-sectional views of a filament feeding mechanism in the advancement stage of a filament feeding cycle in accordance with the embodiment of the invention shown in FIG. 2.
Figure 3B:
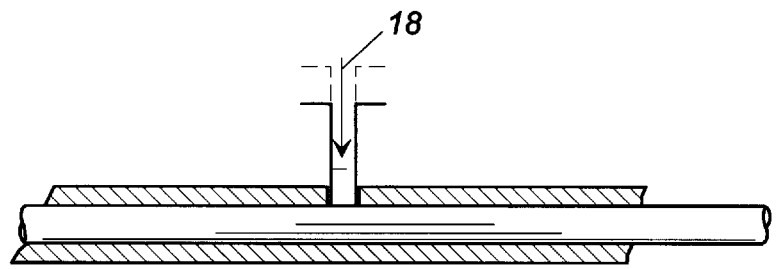
Figure 3C:
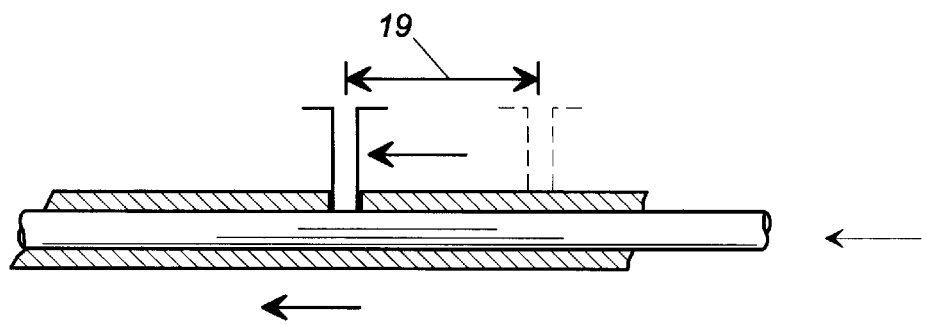

FIG. 3A shows a cutout window 16 in the proximal section of inner cannula 14. Cutout window 16 exposes a small section of filament 5 and allows actuating pad 17 to couple filament 5 and inner cannula 14 to an actuator mechanism 502 (shown in FIG. 5). Actuating pad 17 is referred to, functionally, as a "gripper." FIG. 3B shows actuating pad 17 depressed in a direction 18 transverse to filament 5 in order to engage it securely. FIG. 3C shows the advancement, by means of the action of actuator mechanism 502 (shown in FIG. 5), of actuating pad 17 to the left, and the advancement, along with actuating pad 17, of both inner cannula 14 and filament 5 such that a length of filament 5 equal to the distance 19 of motion of actuating pad 17 is urged into the body tissue.

FIGS. 4A and 4B illustrate the next step of the filament feeding action, the reset part of the cycle, wherein actuating pad 17 is retracted from contact with filament 5 and is urged proximally, in retrograde direction 404, such that inner cannula 14 and actuating pad 17 return to their original proximal position. In a preferred embodiment of the invention, inner cannula 14 has a distal segment 408 and a proximal segment 410, separated by containment spring 412. The direction 406 of retraction of the distal segment 408 of inner cannula 14 is referred to as the retrograde direction. During the reset part of the filament feeding cycle, the filament 5 itself is prevented from coming back out of the body tissue by means of friction brake 402, located proximally to actuating pad 17, which secures filament 5 within the proximal segment 410 of inner cannula 14. Retraction of distal segment 408 of inner cannula 14 is achieved, in a preferred embodiment of the invention, by means of the force supplied by containment spring 412 in compression. The feeding action described allows a high force per unit cross-sectional area to be applied in advancing filament 5 into the body tissue while a lower force is supplied by containment spring 412 to retract the distal segment 408 of inner cannula 14.

Figure 5:
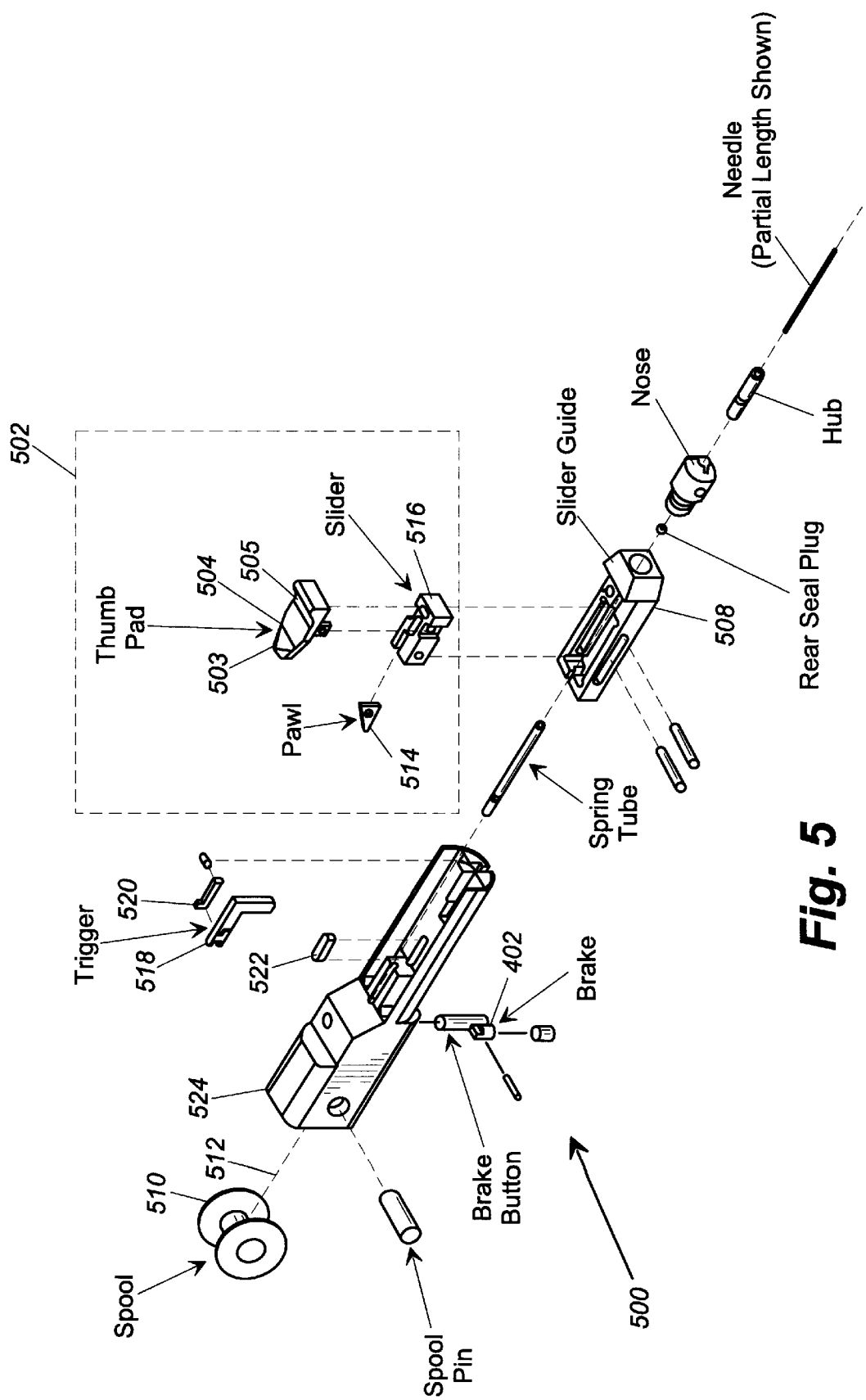
FIG. 5 shows an exploded view of a filament feeding mechanism according to an embodiment of the invention.

Referring now to FIG. 5 wherein the components of a filament feeding mechanism, designated generally by numeral 500, are shown in exploded view. Actuator mechanism 502 is shown to comprise a thumb pad 504 which the physician uses to advance slider 506 forward to a stop in the slider guide 508. By pressing on distal part 505 of thumb pad 504, the physician causes activator pad 17 (shown in FIGS. 4A and 4B) to come into contact with filament 5 (shown in FIG. 4A), and, as he also urges thumb pad 504 forward, he feeds a discrete amount of filament 5, paid off of spool 510 along feed axis 512, into the body tissue, according to the mechanical principle described above with reference to FIG. 3. In an alternate embodiment, the actuation of filament advancement is accomplished by means of an electrical stepper, using mechanical principles known to persons having ordinary skill in the art. The amount of filament fed in each advancement step of the feeding cycle is, typically, on the order of 5 mm. However, design and adjustment of filament feeding mechanism 500 can provide for a longer or shorter length of filament to be fed in each advancement step, indeed, any desired length of filament may be provided per advancement step. To reset the mechanism for the next feeding, the physician depresses the proximal part 503 of thumb pad 504, thereby freeing pawl 514 from a ratchet rack 522 contained in a body 524, and allowing thumb pad 505 and distal segment 408 of internal cannula 14 (shown in FIG. 4B) to retract, according to the principle discussed above with reference to FIGS. 4A–4B. Since the actuating pad 17 is now held up away from the filament 5 and since the suture is held in its forward position by brake 402, the length of filament previously fed remains in the body tissue.

Figure 6:
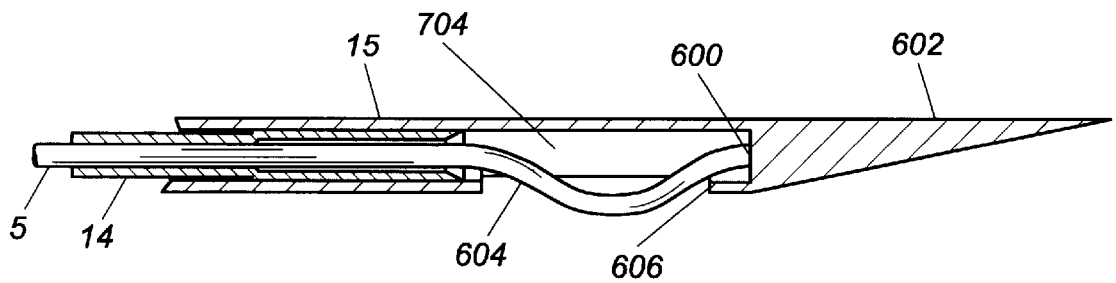
FIG. 6 is a cross-sectional view of the distal tip of a filament feeding mechanism in accordance with an embodiment, of the invention.

FIG. 6 shows a cross sectional view of the distal tip of a filament feed mechanism, according to a preferred embodiment of the invention. It has been found that if the tip 600 of the filament 5 itself is allowed to push straight into the body tissue at the start of the procedure, it can occasionally penetrate the tissue and travel further ahead than clinically indicated, and, instead of remaining in the area surrounding tip 602 of outer cannula 15 and creating the intended localization of filament for purposes of tissue bulking, vas occlusion, or any of the other clinical purposes of filament localization. A solution to this problem, according to a preferred embodiment of the invention, is to provide cutout window 604 in outer cannula 15, immediately proximally to tip 602. As the filament is urged forward, according to the feeding method described above, or otherwise, it bends and then buckles toward the only opening in the area: window 604. Thus the filament enters the body tissue in a gentle sideways manner, presenting to the tissue an area large enough that the force per unit area is insufficient to shear the tissue and to cause inadvertent penetration. Once a filament coiling process is started in this manner, the implanted filament remains within the target region of the body. In order to point the outer cannula window 604 in the direction in which the filament is to be applied to the tissue, the outer cannula 15 is fully rotable about its axis in fixed increments, typically 45-degree increments. A ball plunger arrangement holds the outer cannula in the chosen orientation, according to mechanical principles known to a person of ordinary skill in the art.

Figure 7A:
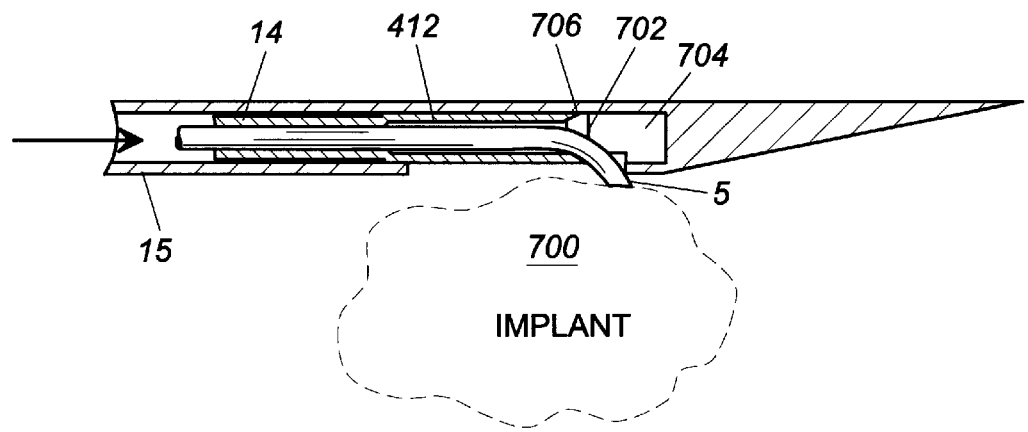
FIGS. 7A and 7B are cross-sectional views of the distal tip of FIG. 6, showing a filament cutting mechanism according to an embodiment of the invention.
Figure 7B:
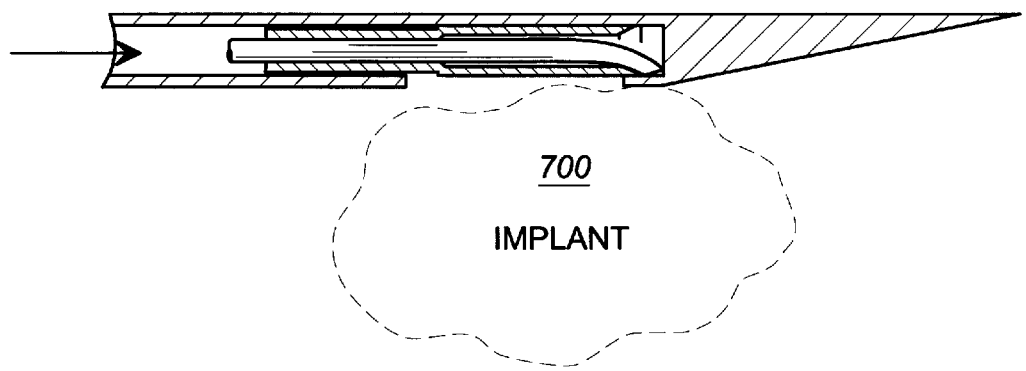

When sufficient filament has been introduced into the body to achieve the requisite tissue bulking or other clinical objective, the physician cuts the filament before withdrawing the device. Thus, in accordance with the present invention, the filament stored in the filament injection device is longer than the amount of filament which is intended to be used in the application at hand. Thus, the desired length may be determined during the course of the procedure and severed after it is deployed into the body of the subject. One method of cutting the filament is described with reference to FIGS. 7A and 7B. In a preferred embodiment of the invention, stop 702 is provided within lumen 704 of outer cannula 16. Distal end 706 of distal segment 412 of inner cannula 14 is provided with a sharpened edge. Thus, when sufficient filament 5 has been injected to constitute the clinically indicated implant 700, distal segment 412 of inner cannula 14 is thrust against stop 702, cutting off filament 5. To allow the inner cannula 14 to advance as far as the cutting stop 702, a trigger 518 (shown in FIG. 5) must be activated by the physician, releasing slider stop 520 (shown in FIG. 5) which, otherwise, prevents the advance of inner cannula 14 to the point of cutting off the filament. In an alternate but equivalent embodiment, the sharpened edge is provided within lumen 704 of outer cannula 16, while, mutatis mutandis, the cutting stop is now provided at the distal edge of inner cannula 14. The cutting action for cutting off the filament remains as described. In an alternate embodiment, the cutting function is achieved by providing a high-tolerance fit of the inner cannula 14 so that when the distal edge 706 of the inner cannula 14 is pushed past distal edge 606 (shown in FIG. 6) of window 604 (shown in FIG. 6), filament 5 is sheared. Shearing of filament 5 may also be achieved, alternatively, through rotation of inner cannula 14 with respect to outer cannula, where shearing surfaces are provided on one or both members, as would be apparent to a person skilled in the art.

Figure 7C:
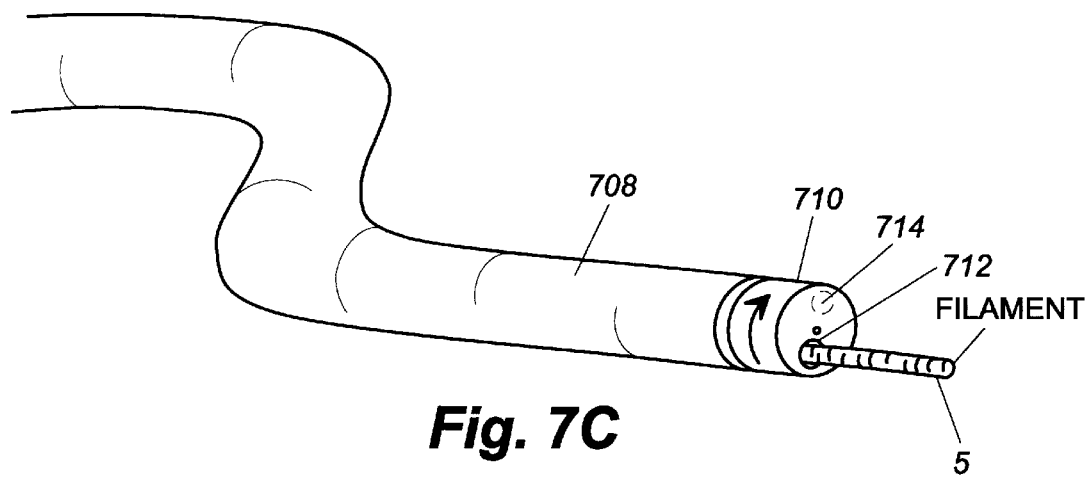
FIG. 7C is a perspective view of the distal tip of a conduit in accordance with an embodiment of the invention showing an alternate filament cutting mechanism.
Figure 7D:
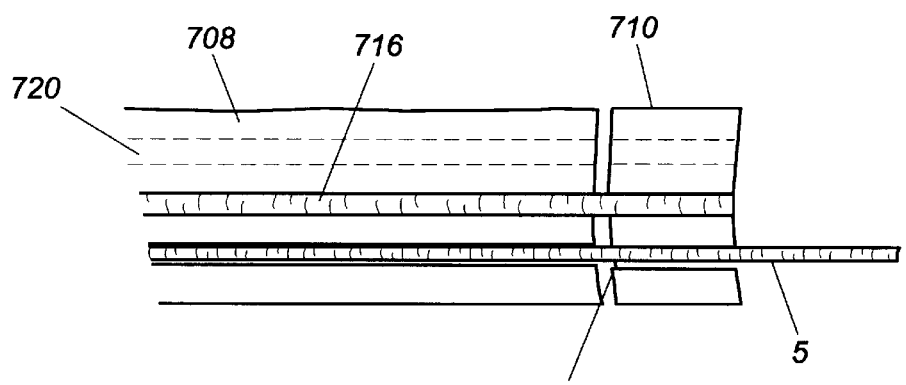
FIG. 7D is a cross-sectional view of the filament cutting mechanism of FIG. 7C.

Another method of cutting the filament is described with reference to FIGS. 7C and 7D. In an alternate embodiment of the invention shown in FIG. 7C, conduit 708, which can be used in conjunction with any of the filament feeding mechanisms described herein, is provided, at its distal end, with a torquable head 710 containing window 712 within distal surface 714. Referring now to the cross sectional view shown in FIG. 7D, torque is transmitted to rotate torquable head 710 via torque wire 716 which runs through conduit 708 so that torque may be applied at its proximal end (not shown). When torquable head 710 is rotated, filament 5 is cut by blade inset 718, such that, upon withdrawal of conduit 708 from the body, the requisite length of filament 5 is left in the body. In one embodiment of the invention, a cannula 720 is provided through conduit 708, parallel to filament 5, so that fluid or a guide wire may be introduce via cannula 720 through port 714 in torquable head 710 into the body region into which filament 5 is being inserted.

Figure 8:
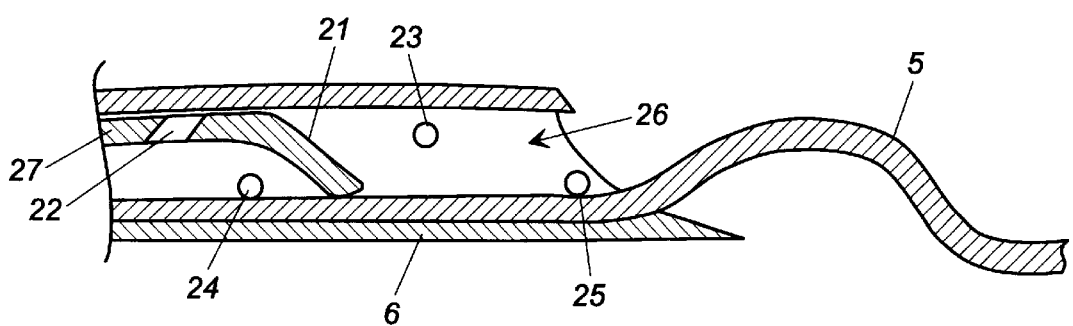
FIG. 8 is a cross-sectional view of an filament feeding mechanism according to an alternate embodiment of the invention.

FIG. 8 shows the detail of how the filament may be advanced into the tissue. Within the lumen 26 at the tip of needle 6, the filament is held in a position against the wall by struts 24 and 25. Shaft 27 has a head 21 and a channel 22 spaced back from the tip of head 21 a small distance. As shaft 27 is advanced, head 21 comes in contract with partial pivot 23 and is forced downward, engaging filament 5. As shaft 27 continues to advance, filament 5 is pushed forward as head 21 subluxes under pivot 23. With the continued advancement of shaft 27, eventually channel 22 aligns with pivot 23, permitting it to spring back into its original shape, disengaging filament 5. Then, as shaft 27 is withdrawn, head 21 rides over pivot 23, losing contact with filament 5 preventing inadvertent withdrawal of filament 5. Finally the cycle is complete when head 21 pops over pivot 23 and snaps back into its original shape and position at the start of the cycle.

Figure 9:
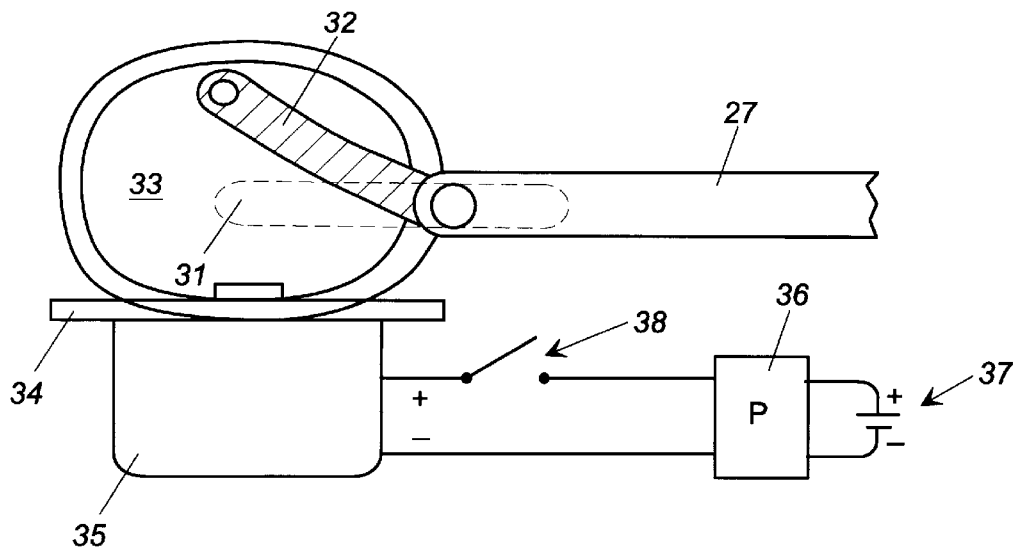
FIG. 9 is a schematic of a powered drive system for cycling the shaft 27 with the touch of a button.

FIG. 9 illustrates a schematic of a powered drive system for cycling the shaft 27 with the touch of a button. When switch 38 is turned on, power to a small motor 35 turns a set of gears 33 and 34 which drive a bar linkage 32 riding in a channel 31. The bar linkage 32 is attached to the shaft 27 at the point within or near the channel 31. Power source 37 may be connected to processor 36 which may be capable of correlating, tracking or controlling 'on-time' as it relates to the mass of filament deposited within the body. Alternatively, those skilled in the art will recognize that various mechanical methods are easily applied which would allow the shaft to be man-powered or mechanically driven.

Figure 10:
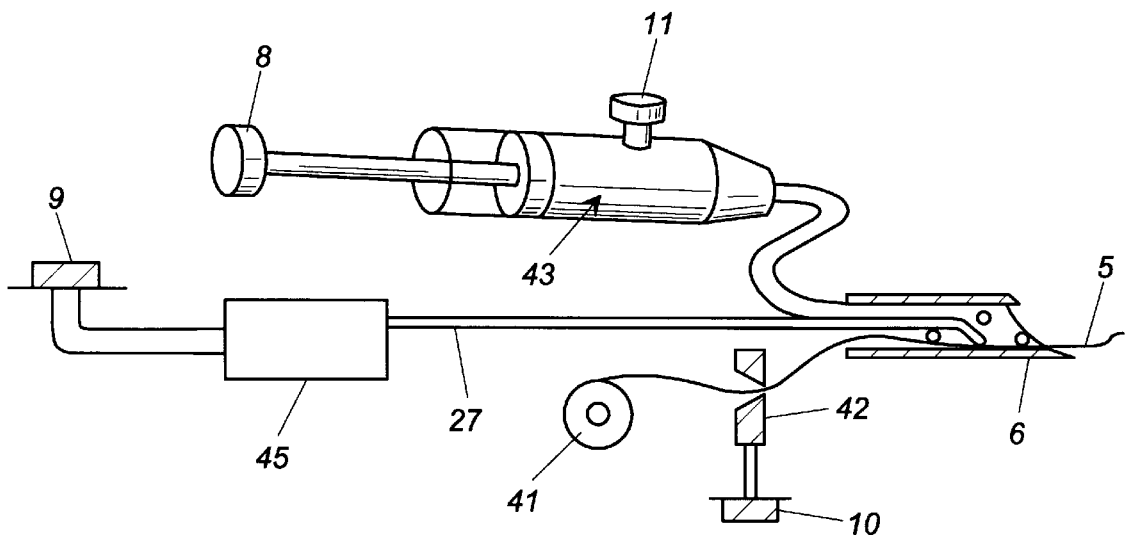
FIG. 10 illustrates a layout of an alternative embodiment of the system.

FIG. 10 illustrates a layout of an embodiment of the system. Fluid control 8 may drive fluid stored in vessel 43 forward through the tip of needle 6. A principal purpose of the fluid is to dilate the space to be occupied by the filament; in this connection, the fluid may be a suitable liquid such as saline, although the fluid may also or alternatively include anesthetic, antibiotic, or other medication. Other methods may also be used for dilation of the space, including inflation of a temporary balloon. Alternatively, the implantation of the filament itself may be used to cause dilation of the space. Further, it is envisioned that an endoscope may desirably be inserted into the space before, during or after the treatment to ensure proper placement. Injection port 11 provides access to vessel 43. Injection control 9 is attached to drive mechanism 45 which is subsequently linked to shaft 27. As discussed earlier, the movement of shaft 27 drives filament 5 forward. Spool 41 stores filament 5 prior to delivery and acts as a filament reservoir as filament 5 is advanced. If only a portion of filament 5 is required, filament 5 may be severed by cutting mechanism 42 activated by cut control 10.

Figure 11A:
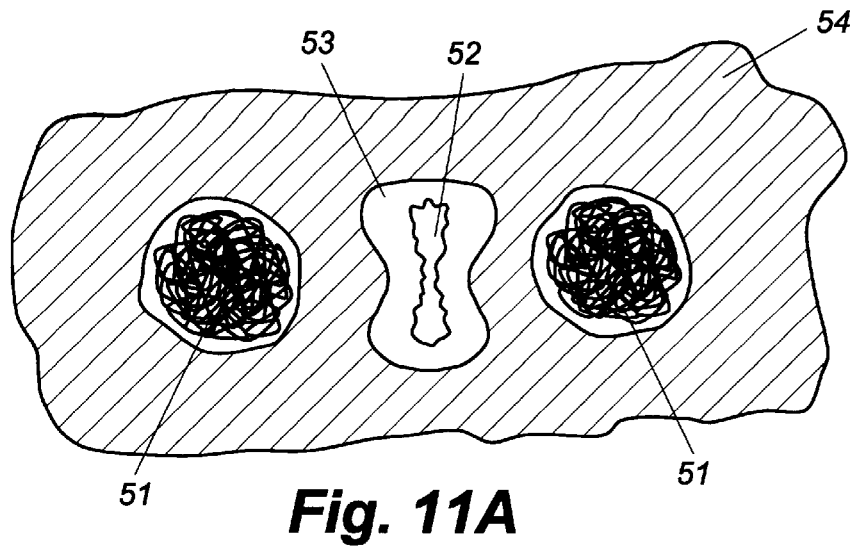
FIG. 11A is a cross section of the result after the device has been used to coapt the walls of a tubular structure within the body.

FIG. 11A is a cross section of the result after the device has been used to coapt the walls of a tubular structure 52, or vas (as defined above), within the body. The tubular structure 52 may be any within the body such as a ureter, urethra, vein, artery, bowel, esophagus, stomach, oropharynx or sphincter. Other body tissue 54 surrounds wall 53 of tubular structure 52. Filament balls 51 have been placed on either side of the tubular structure to create an increase in resistance to flow, provide a site for local drug delivery or support internal structures such as valves. Placement of filament balls 51 within exterior body tissue 54 is shown by way of example, while placement within or proximal to wall 53 is also within the scope of the invention.

Figure 11B:
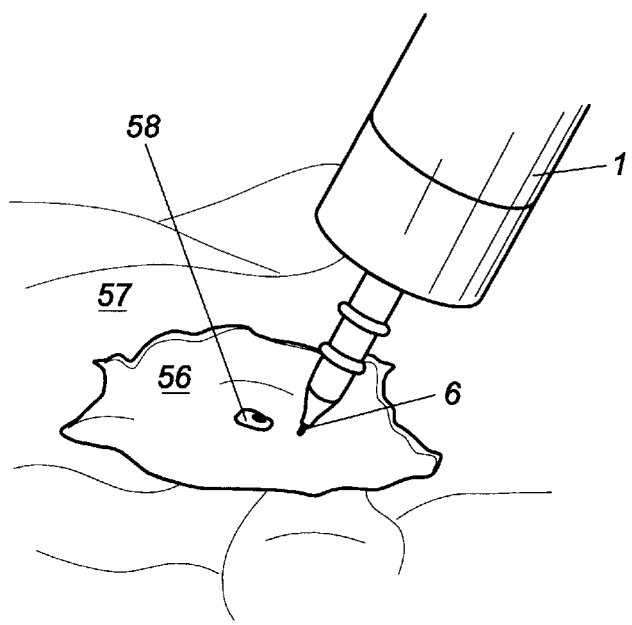
FIG. 11B illustrates an embodiment of the invention for treatment of an ulcer.

FIG. 11B illustrates another embodiment of the invention, in which filament injection device 1 is applied in the treatment of an ulcer such as a peptic ulcer of the duodenum, stomach, or lower esophagus. Conduit 6 is shown supplying filament (not shown) into crater 56 of ulcerated mucosa 57 surrounding blood vessel 58. By inserting the fiber into the vicinity of blood vessel 58, it is possible to stop the supply of blood to the ulcer.

Figure 12:
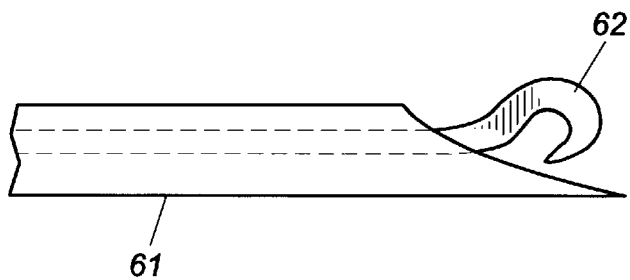
FIG. 12 illustrates an embodiment of the invention for removing a filament in the body after it has been placed.

FIG. 12 illustrates an embodiment of the invention for removing a filament in the body after it has been placed. Cannula 61 is advanced into the center of the filament ball and then hook 62 is pushed forward. Once a strand of the filament has been captured or snagged by the hook 62, the filament and the device may be withdrawn.

Figure 13A:
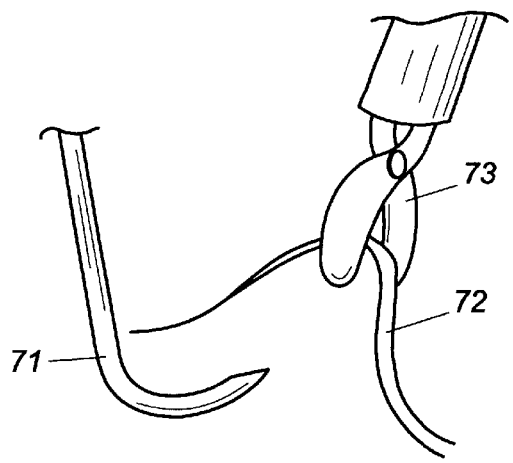
FIGS. 13A–13C illustrate use of the device of FIG. 1 for passing suture through and around tissue, and, in FIG. 13C, for creating a series of linked loops.
Figure 13B:
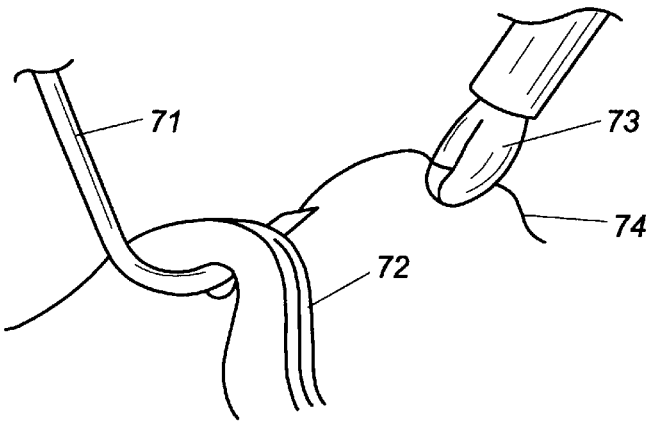
Figure 13C:
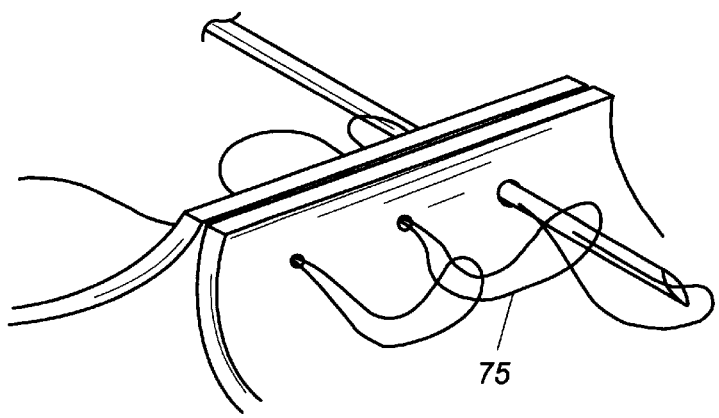

The present invention may be used for purposes other than bulking of tissue. In particular, the device of the present invention may also be used for the delivery of suture for purposes such as sewing, ligation, and anastomosis. In this mode, the device may be passed into and through tissue, advancing a singular loop of suture before being pulled back. As seen in FIGS. 13A–13C, the procedure may permit the suture to be passed through and around tissue without the requirement of manipulating a loose needle. Here needle 71 is passed through tissue 72 with the aid of grasper 73. Once through the tissue, filament 74 is advanced and grasped by grasper 73; then the needle 71 may be withdrawn. After the filament has been deployed as desired, the filament may be severed, and once the filament is severed, a knot may be tied. Another use is shown in FIG. 7C. Here, several insertions of needle 71 can be performed to create a series of linked loops 75 which can ultimately be tensioned and tied.

FIG. 14 illustrates the mechanism through which particles may be injected into the body, in accordance with another embodiment of the invention, in order to accomplish the same purposes as taught in this specification with respect to the injection of filament. Again, as in the case of filament, the particle may be one of any of the currently available biocompatible materials, including but not limited to silk, plastic, polymer, metal, cells, collagen, bone or other material described above in connection with the definition of the term "filament". Specifically, as with the filament, the material may also be one of any available suture materials such as polyglycolic acid (PGA), polytetrafluoroethylene (PTFE), DACRON™, polypropylene, nylon polyester, silk, polybutylester, stainless steel, titanium, chromic gut, polybutylester, cotton, or silver. Here, particles 80 are shown being injected into a created cavity 86 within the body 87. Particles 80 are passed down the shaft 81 along with a pressurized fluid 83 from storage chamber 88 propelled by pressure source 84. The fluid is then withdrawn via channel 82 by suction source 85. The pressure and suction sources may be manually activated or may be electronically controlled or otherwise controlled. The pressurized fluid may be also a gas like $CO_2$, but may also be saline, dextrose, antibiotic or other biocompatible agent that acts either passively to assist the particles to reach their destination, or performs another purpose such as providing antibiotic protection, activating the particles once in place, or providing a means through which the particles may be held in one place. The particles may be of any size which permits them to be introduced down the shaft of a cannula, catheter or needle.

Figure 15A:
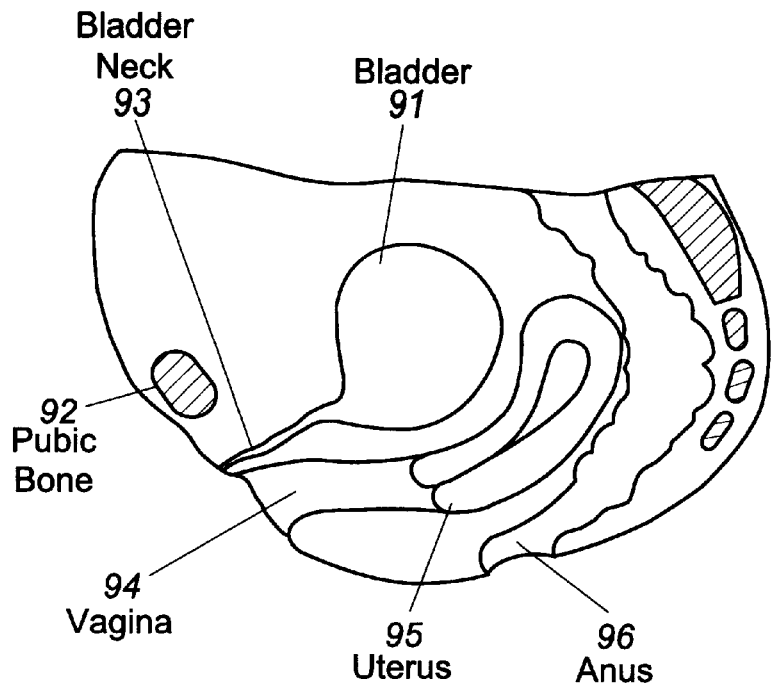
FIGS. 15A and 15B show respectively a descended bladder of a female subject and the same bladder after it has been elevated by use of a filament implanted in accordance with an embodiment of the invention.
Figure 15B:
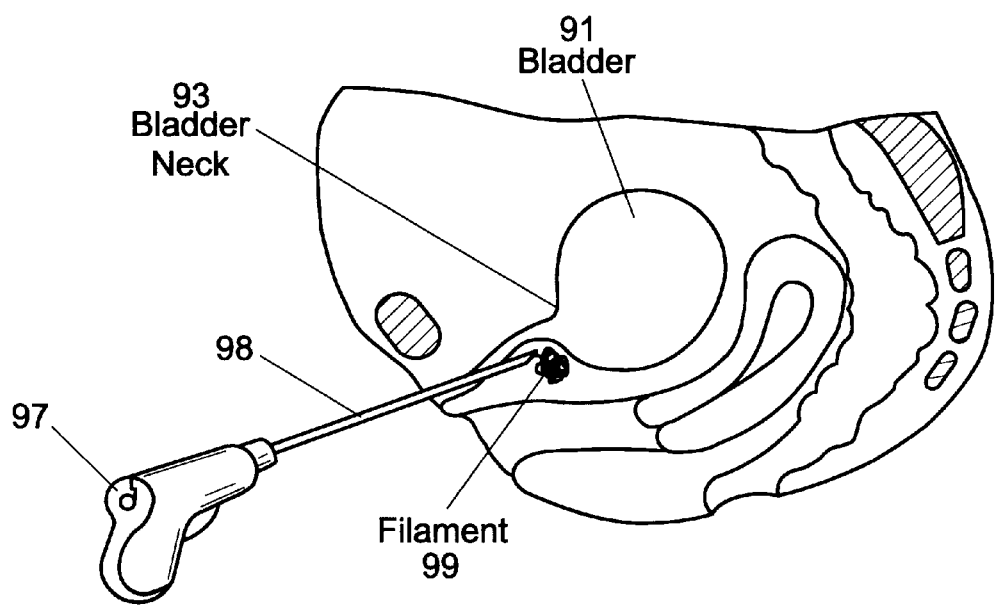

FIGS. 15A and 15B show respectively a descended bladder of a female subject and the same bladder after it has been elevated by use of a filament implanted in accordance with an embodiment of the invention. In these figures the bladder 91 and bladder neck 93 are shown in relation to the pubic bone 92, the vagina 94, uterus 95, and anus 96. In accordance with this embodiment, as shown in FIG. 15B, filament 99 is implanted in tissue so as to provide elevation of the bladder in the region of the bladder neck 93. The filament 99 is inserted using cannula 98 to which is affixed delivery tool 97. Detailed descriptions of the delivery tool 97 are provided below. It will be appreciated that other organs and tissue may be similarly supported or relocated using similar techniques.

Figure 16:
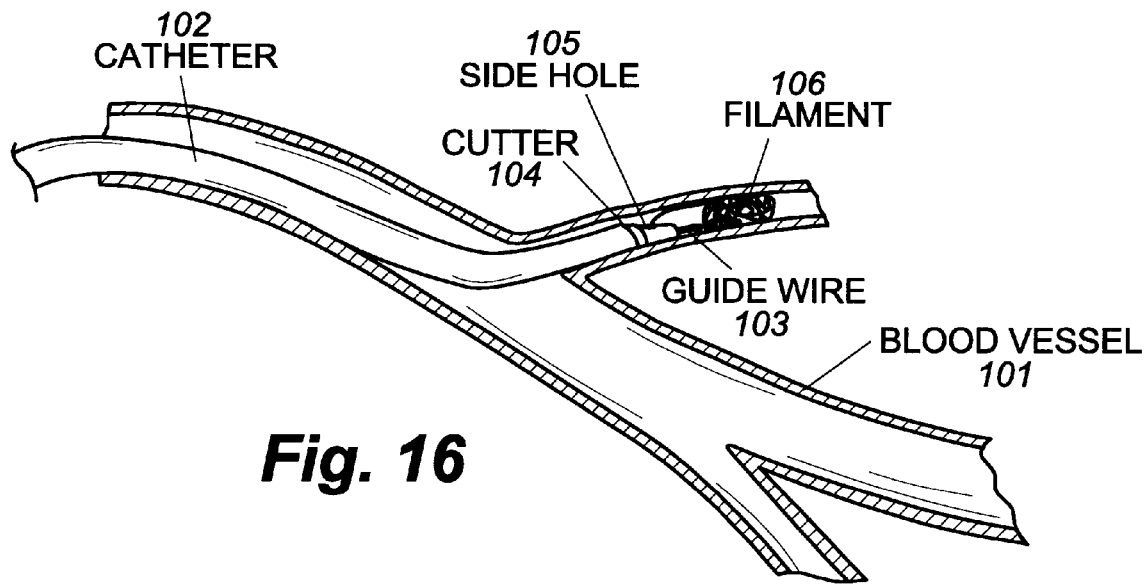
FIG. 16 shows an embolism that has been achieved in a blood vessel by means of a filament implanted in accordance with an embodiment of the invention.

FIG. 16 shows an embolism that has been achieved in a blood vessel by means of a filament implanted in accordance with an embodiment of the invention. Here filament 106 has been inserted to create an embolism in the blood vessel 101. Insertion of the filament is achieved first by appropriate placement of guide wire 103 in a manner known in the art. Catheter 102 is equipped with a cutter 104 and a side hole 105 from which emanates the filament 106. After an appropriate length of filament has been implanted in the blood vessel 101, the cutter 104 is used to cut the filament at the point where it emanates from the catheter, and the catheter and guide wire are thereupon removed. A technique similar to this may be utilized in other tissue to prevent flow or leakage.

Figure 17:
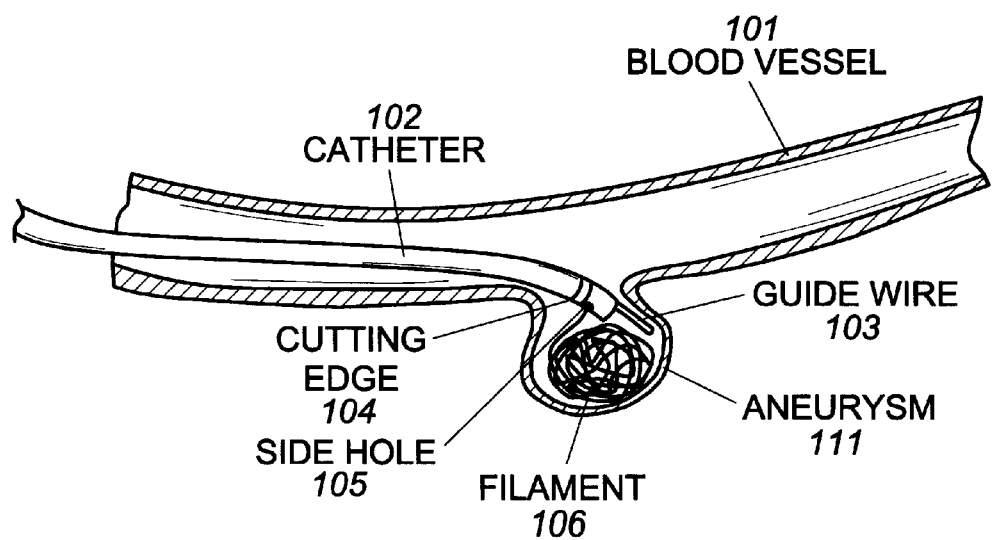
FIG. 17 shows an aneurysm that has been filled by means of a filament implanted in accordance with an embodiment of the invention.

FIG. 17 shows an aneurysm that has been filled by means of a filament implanted in accordance with an embodiment of the invention. In this figure filament 106 is used to fill aneurysm 111 in blood vessel 101. Again insertion is achieved utilizing guide wire 103 over which catheter 102 is inserted. The catheter 102 is used to carry the filament 106, which emerges from side hole 105 and is cut, after a desired length has been implanted, by cutter 104.

FIGS. 18A through 26 illustrate various embodiments of the invention for achieving the movement of a filament along a desired path so as to permit implantation of the filament. It will be appreciated that these embodiments, which provide an engine for the advance of filament in a catheter, may be incorporated in a variety of delivery tools. One type of delivery tool may be in the form of a completely hand-held unit, which includes a spool or cartridge of filament, the filament-advance engine, as well as a fitting to receive a catheter or other insertion device. The entire unit may be disposable or it may be provided with features making it able to withstand sterilization in an autoclave or by other means. Similarly, it is within the scope of the present invention to put the filament-advance engine in a first case, along with a cassette or spool of filament, and permit the case to be placed on a table or otherwise suspended or mounted in a convenient location for use. In this connection, there may be attached to the case a disposable cannula for carrying the filament to the site of the operation. The cannula may be fitted with a suitable handle and control arrangement, as well as a tip. The cannula, handle and tip may all be implemented as disposables or alternatively as sterilizable items. The filament advance engine may be motor driven or hand driven. In the event that it is hand driven, power to the device may be provided by successive squeezes of a trigger or lever against a handle for the tool; the extent of the squeeze may regulate the extent of the advance of the filament.

As discussed above, the filament may be a monofilament made, for example, of a suitable polymer such as nylon, polybutylester, or polypropylene. Alternatively the filament may be braided. In the case of a braided filament and in some instances in the case of a monofilament, the flexibility of the filament may make it difficult to advance, even in a cannula. Accordingly, in an embodiment of the invention, the filament is treated with a suitable stiffening agent, typically at a time prior to placement of the filament in the delivery tool. This stiffening agent is preferably made up of an absorbable material, such as starch, but it is within the scope of the invention to utilize other materials that provide requisite stiffness and avoid the irritation of tissue. The stiffness of a filament may also be varied through temperature-effects in situ, such as by use of the temperature-dependent properties of polymers and other materials, as known to persons skilled in the art.

The filament may be provided to the delivery tool in a spool or other convenient form. In this respect, it should be noted that it is typical for many filament materials to have some shape memory, and the manner in which the filament is spooled can affect the manner in which the filament responds as it emanates from the delivery tool and even as it is being advanced through the delivery tool. Accordingly the spooling of the filament may be implemented in a manner designed to provide characteristics suitable for the particular implantation task at hand. Where it is desired, for example, to have the filament tightly occupy a small volume, the filament may be wound on a spool of small diameter and heated in place on the spool to cause memorization of the small-radius associated with the spool. Note that the small-radius may be retained in shape memory even if the filament must be subsequently be rewound onto a different spool for insertion into the delivery tool. It is also possible, of course, to sterilize the filament after it has been wound onto the spool.

Figure 18A:
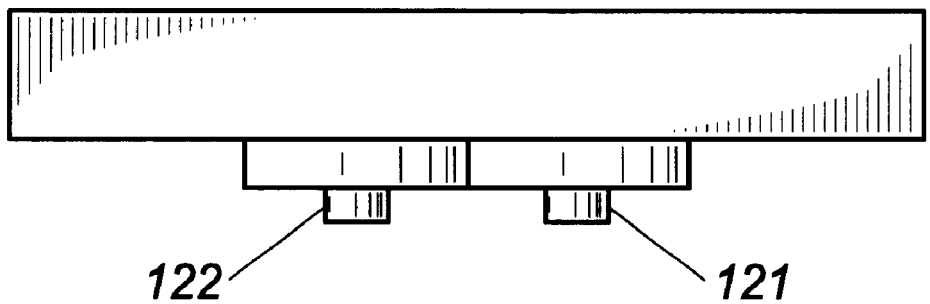
FIGS. 18A and 18B illustrate an embodiment for achieving movement of a filament utilizing a pair of conveyor belts symmetrically engaged against the filament.
Figure 18B:
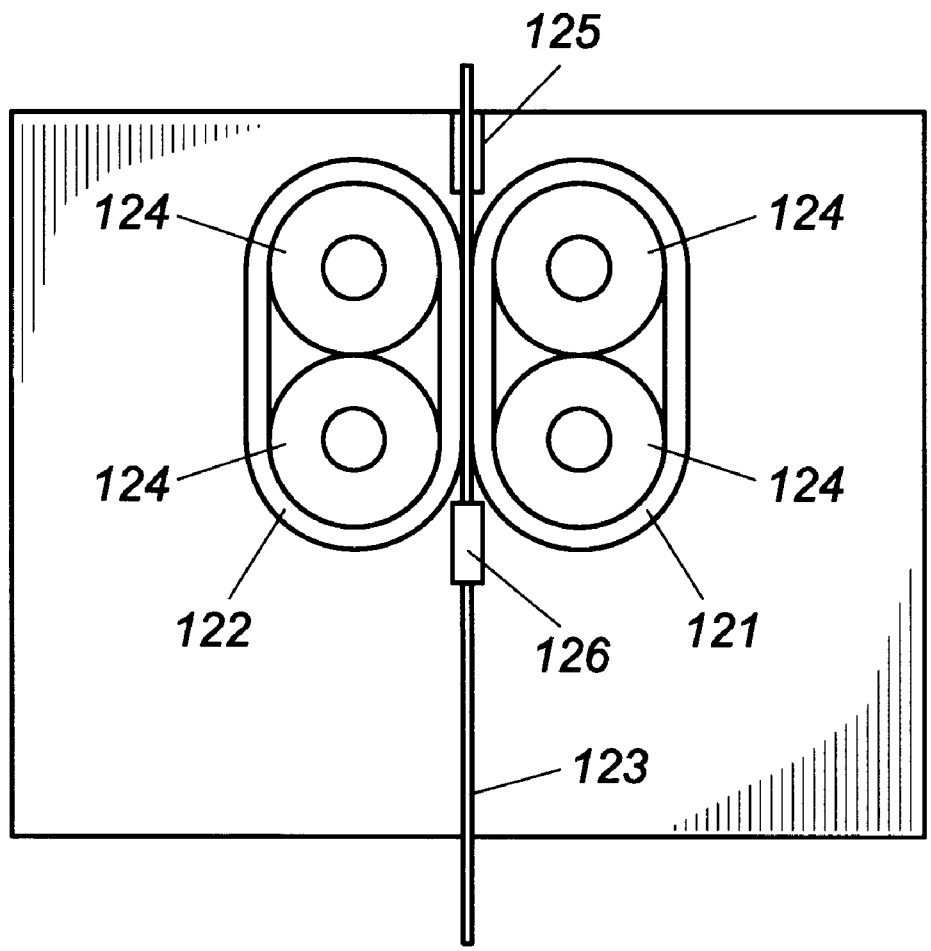

FIGS. 18A and 18B illustrate an embodiment for achieving movement of a filament utilizing a pair of conveyor belts symmetrically engaged against the filament. Here the conveyor belts 121 and 122 engage against the filament 123. The belts are driven by one or more of the pulleys 124 about which they are mounted. The filament 123 is fed through an input conduit 126 into an output conduit 125 that is located preferably close to the location where the filament emerges from the pair of belts so as to prevent bunching. The outer diameter of output conduit 125 may be ground down to allow close proximity between output conduit 125 and conveyor belts 121 and 122.

Figure 19:
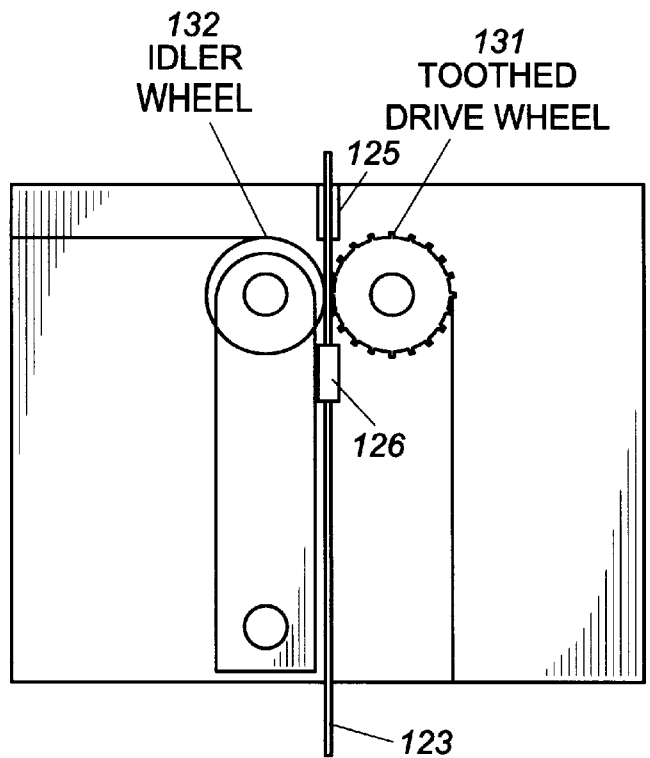

FIG. 19 illustrates an embodiment for achieving movement of a filament utilizing a toothed drive wheel against which the filament is engaged by an idler wheel. The toothed drive wheel is shown as item 131 and the idler wheel as item 132. Also shown are the input conduit 126 and the output conduit 125. The outer diameter of output conduit 125 may be ground down to allow close proximity between output conduit 125 and drive wheels 131 and 132.

Figure 20:
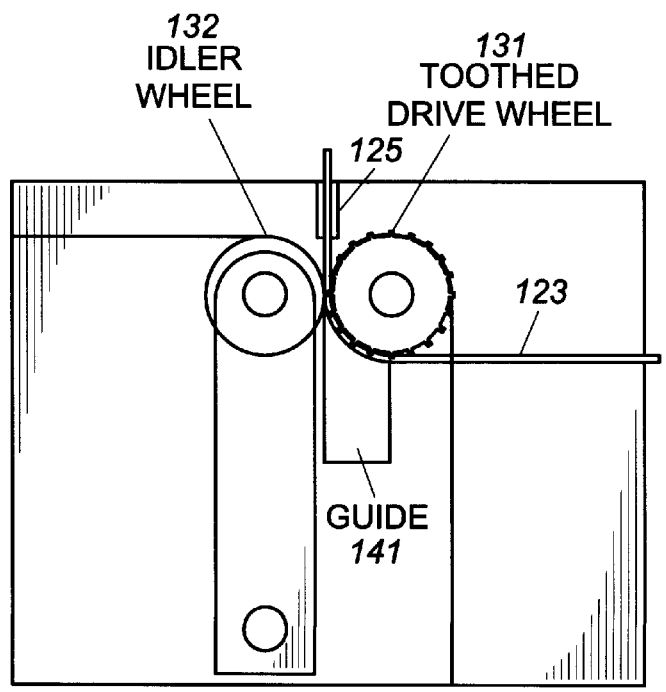

FIG. 20 illustrates an embodiment, similar to that of FIG. 19, utilizing a toothed drive wheel against which the filament is engaged by an idler wheel, but wherein the filament is also engaged against the drive wheel by a guide having an arcuate surface that general conforms to the radius of the drive wheel. Here the guide is shown as item 141, and it replaces input conduit 126. The advantage of this arrangement is that it increases the length of the filament 123 that is engaged by drive wheel 131 and therefore ensures better traction by the drive wheel 131.

Figure 21A:
FIGS. 21A and 21B illustrate and embodiment, similar to that of FIG. 19, utilizing a toothed drive wheel against which the filament is engaged by an idler wheel, but wherein the idler wheel is soft.
Figure 21B:
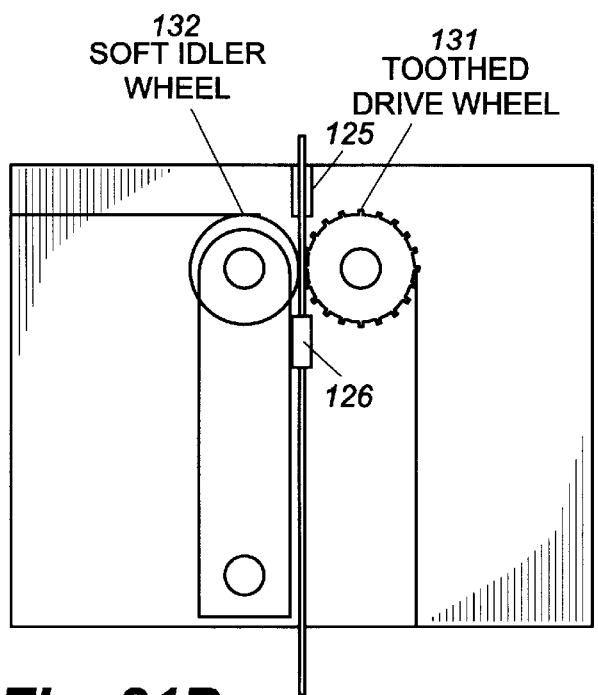

FIGS. 21A and 21B illustrate an embodiment, similar to that of FIG. 19, utilizing a toothed drive wheel 131 against which the filament is engaged by an idler wheel 132, but wherein the idler wheel at 132 is soft.

Figure 22:
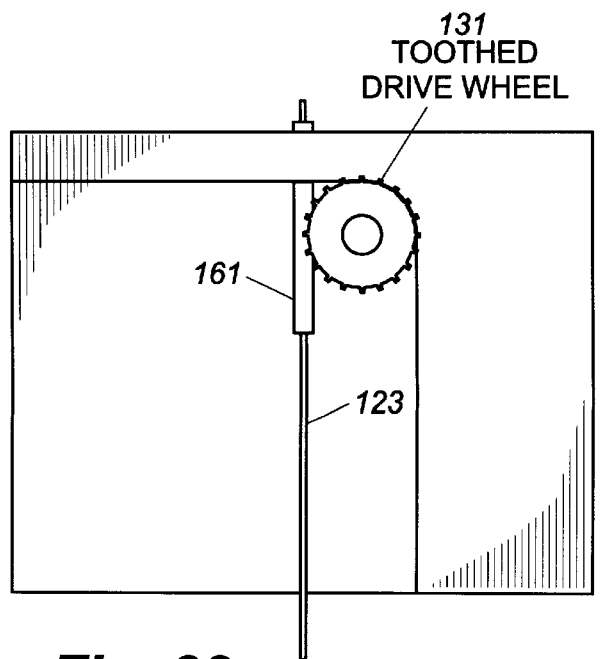

FIG. 22 illustrates an embodiment for achieving movement of a filament utilizing a toothed drive wheel against which the filament is engaged by a tubular guide. In this figure the drive wheel 131 operates through a slot formed in the tubular guide 161. This embodiment has the advantage of achieving a complete merger of the input and output conduits.

Figure 23A:
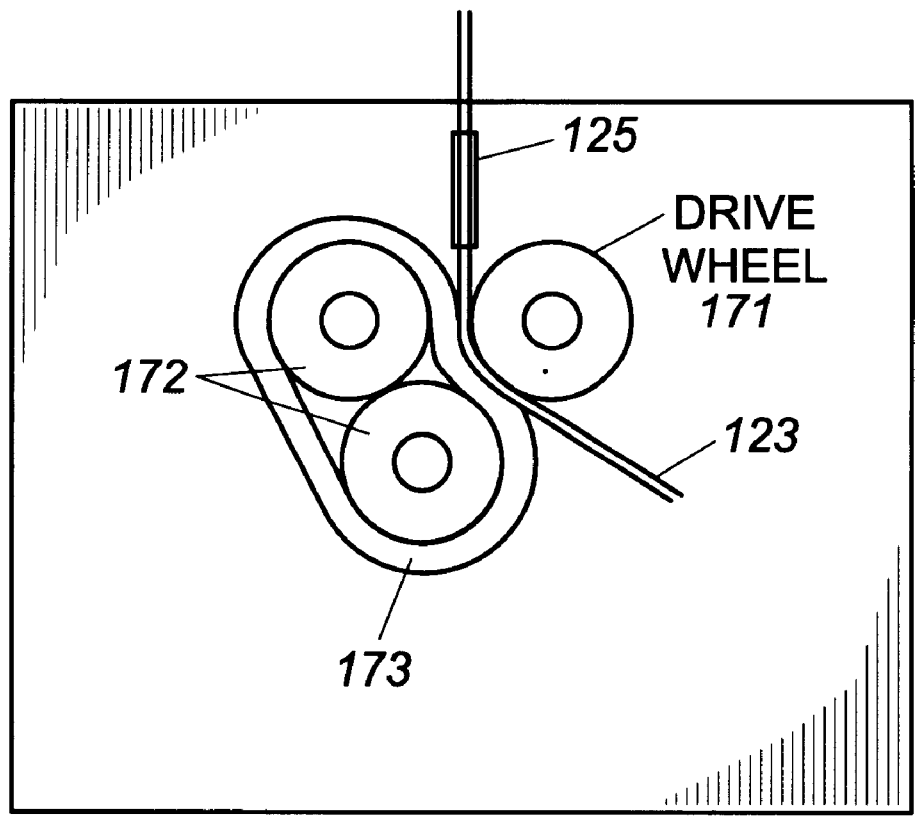
FIGS. 23A and 23B illustrate an embodiment for achieving movement of a filament utilizing a drive wheel against which the filament is engaged by an idler belt.
Figure 23B:
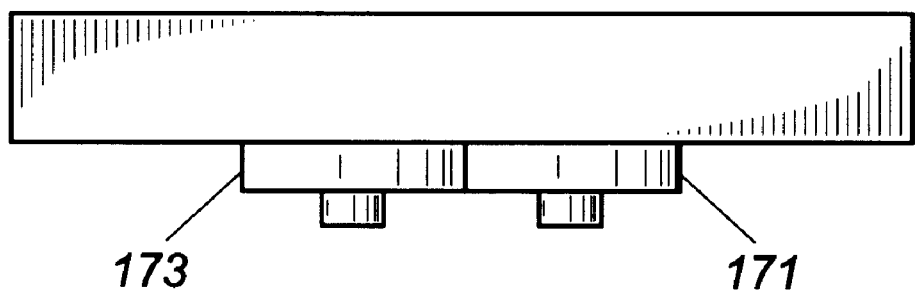

FIGS. 23A and 23B illustrate an embodiment for achieving movement of a filament utilizing a drive wheel against which the filament is engaged by an idler belt. In this figure the drive wheel 171 is shown to engage the filament 123 against belt 173 that is disposed around pulleys 172. The filament emerges through exit conduit 125.

Figure 24A:
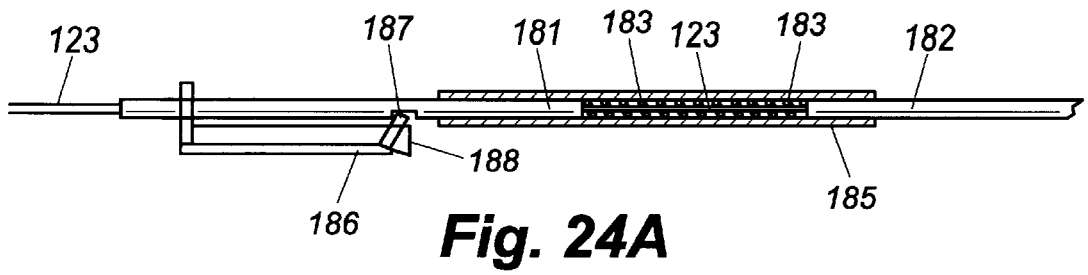
FIGS. 24A through 24E illustrate an embodiment for achieving movement of a filament utilizing a pair of axially reciprocating tubular members, within which the filament is disposed, in conjunction with a periodically clamping finger.
Figure 24B:
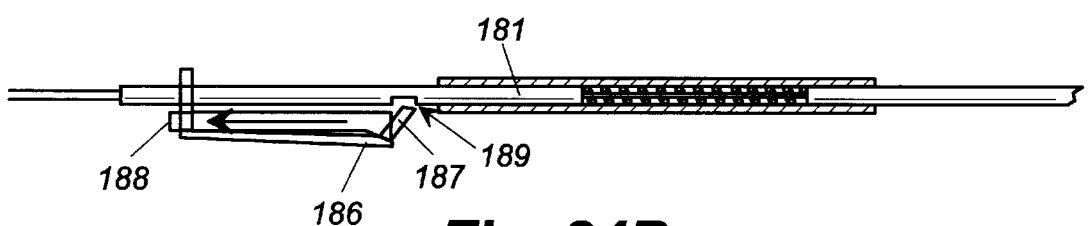
Figure 24C:
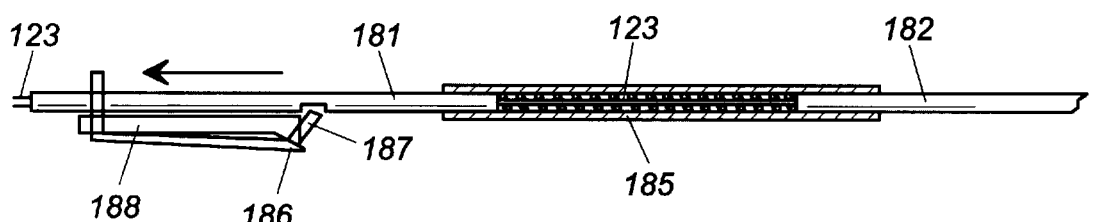
Figure 24D:
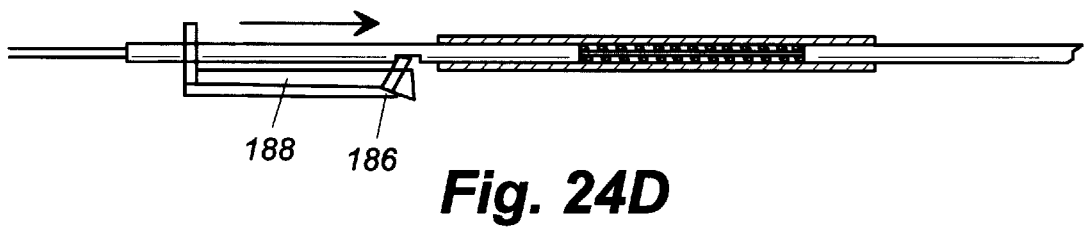
Figure 24E:
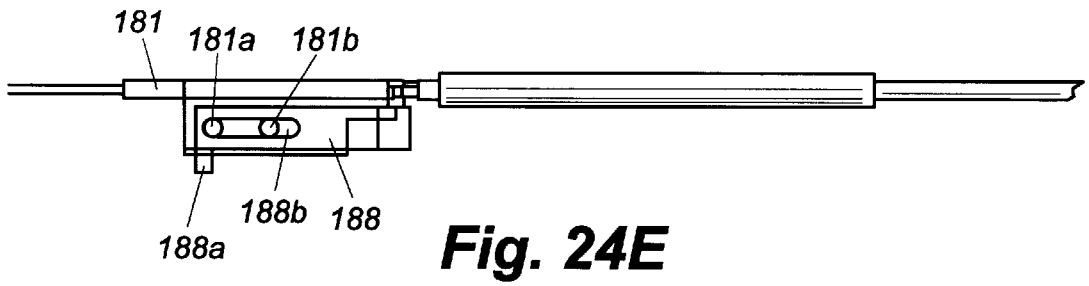
Figure 25A:
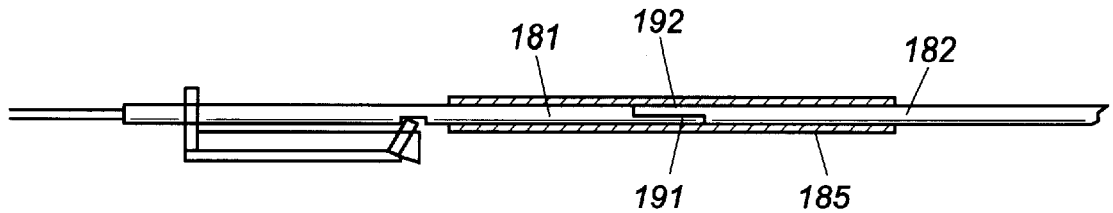
FIGS. 25A through 25E illustrate an embodiment similar to that of FIGS. 24A through 24E but in which the coil springs of the latter figures are supplanted by complementary mating extensions of the tubular members.
Figure 25B:
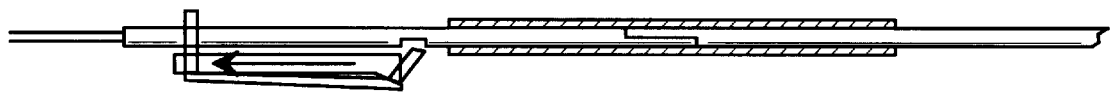
Figure 25C:
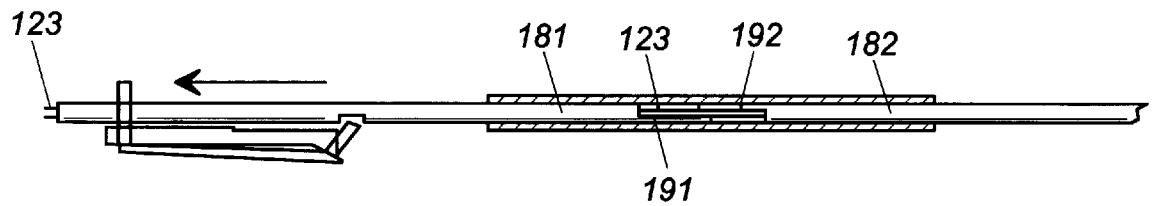
Figure 25D:
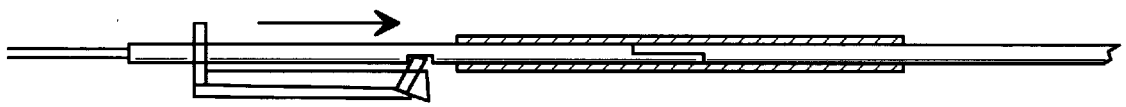
Figure 25E:
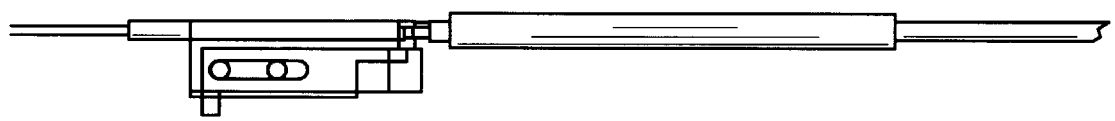

FIGS. 24A through 24E illustrate an embodiment for achieving movement of a filament utilizing a pair of axially reciprocating tubular members, within which the filament is disposed, in conjunction with a periodically clamping finger. In these figures the tubular members 181 and 182 operate within sleeve 185. Tubular member 181 is caused to move within the sleeve 185 carrying the filament 123 with it during the feeding phase. The finger 186 is spring loaded to cause the tip 187 of the finger to press against the filament 123 in channel 189 of the tubular member 181. During the reset phase, filament 123 is trapped from retrograde movement by finger 186. In FIG. 24A, the tubular member 181 is fully advanced, having just completed a stroke. In FIG. 24B, the tip 187 of finger 186 has been caused to move away from the filament 123 in channel 189 owing to action of the sliding cam 188. The disengagement of the finger 186 from the filament permits the tubular member 181 to slide axially to the left in sleeve 185 without causing any motion of the filament in a leftward direction. The assembly consisting of the tubular member 181 and the finger 186 with its cam 188 is thus shown fully retracted in FIG. 24C. In FIG. 24D the cam 188 has been slid to the right, permitting the finger 186 to engage the filament 123 at the tip 187 of the finger. The finger so engaged is shown in FIG. 24D. At this point the tubular member and finger assembly can then advance to the right as shown in FIG. 24A. In order to maintain the shape of the filament 123, between the termination of the tubular members 181 and 182 is a spring 183 within the sleeve 185. These springs surround the filament and tend to reduce any bowing of the filament that would prevent transmission of force along its length. FIG. 24E shows the assembly of FIGS. 24A through 24D rotated 90°. Here it can be seen that the sliding cam 188 may receive reciprocating power at tab 188*a*. A slot 188*b* is formed in a portion of the cam through which protrude posts 181*a* and 181*b* that are coupled rigidly to the tubular member 181. Accordingly, when the cam is urged to the right and when post 181*a* hits the leftmost limit of slot 188*b*, the power provided at tab 188*a* will cause the tubular member 181 to move to the right. When the post 181*b* encounters the rightmost portion of slot 188*b*, the tubular member 181 will be moved to the left. This arrangement permits the same reciprocating power at tab 188*a* to actuate both the cam 188 and the tubular member 181. As shown in certain other embodiments, it may be necessary or desirable to provide a suitable arrangement for applying a slight resistance to leftward motion of the filament when the tubular member 123 is undergoing retraction from the fully advanced position.

FIGS. 25A through 25E illustrate an embodiment similar to that of FIGS. 24A through 24E but in which the coil springs of the latter figures are supplanted by complementary mating extensions of the tubular members. In this case the tubular member 181 includes the extension 191 and the tubular member 182 includes the extension 192. The strokes for advancing the filament in the case of FIGS. 25A through 25D correspond to the strokes described previously in connection with FIGS. 24A through 24D. Similarly FIG. 25E corresponds to FIG. 24E. It can be seen in FIG. 25C that as the tubular members 181 and 182 are separated, some guidance for the filament 123 is provided by the extensions 191 and 192 of the tubular members 181 and 182 respectively. Although only a single pair 191 and 192 of extensions are shown, it is within the scope of the present invention to provide a plurality of extensions to each of the tubular members 181 and 182 in such a way that the extensions meet with each other when the tubular members 181 and 182 are fully advanced to provide the effect of a single conduit; and when the tubular members are separated, a plurality of extensions are present around the end of the tubular member to provide support for the filament.

FIGS. 26A and 26B illustrate an embodiment for achieving movement of a filament utilizing a pair of arms that are caused to reciprocate axially while being alternately opened and closed at the opposite ends of each stroke. In this figure are shown arms 201 and 202 that include tips 203 and 204 respectively for pinching filament 123. Cam assembly 205 is arranged to cause successive opening and closing of the arms 201 and 202 and therefore of the tips 204 and 203. The cam assembly 205 is also configured to cause reciprocating motion of the arm assembly in the left-right direction, that is, in the direction of the length of filament 123. Furthermore, the cam assembly 205 is configured so that a cycle of operation causes the tips 203 and 204 to grab the filament 123 when the arm assembly is in its leftmost position and to retain grip on the filament until the arm assembly has reached its rightmost position. At this position, on the arm assembly is caused to open, whereupon grip of the tips 204 and 203 on the filament 123 is released. In FIGS. 26A and 26B can be seen spool 207 of material constituting filament 123 as well as output conduit through which the filament 123 runs after exiting from the tips 204 and 203. In the output conduit 207 is a channel into which protrudes pawl 206. The pawl is angled in such a way that it offers little resistance to forward motion of the filament, but offers considerable resistance to rearward motion of the filament (forward motion being to the right). If it is desired to retract the filament 123 the arms 201 and 202 may be opened and the spool 207 may be powered to effectuate rewinding, in which case the pawl 206 may also be optionally disengaged from the filament. Alternatively, the spool 207 may be driven in reverse through a clutch arrangement and the advance mechanism constituting the two arms may be run backwards.

In the case of the filament-advance engines described above, it is possible to monitor a number of parameters including the number of revolutions of the filament spool, or (directly) the length of filament being unspooled, as well as the number of reciprocations or drive movements associated with attempts at moving the filament. The drive movements can be matched against actual filament movement in order to determine whether slippage is taking place. If it is determined that slippage is present, an alarm state may be entered to permit appropriate corrective action.

FIGS. 27A through 30D illustrate embodiments of the invention in which a region proximate to a tip of a cannula carrying a filament is provided with an arrangement, for cutting the filament, utilizing a concentrically disposed member and a window in both members through which the filament is placed and severed.

FIGS. 27A and 27B illustrate an embodiment wherein the outer member is pulled proximally with respect to the inner member to achieve cutting. In FIG. 27A there is shown inner member 212 in relation to outer member 213. Filament 211 is carried in the lumen of the inner member 212 and emanates from window 214. In FIG. 27B the outer member 213 is pulled proximally with respect to the inner member 212 so that a scissors action results from the passage of edge 214 on the outer member 213 by the edge 215 of the inner member 212. The result is the cutting of filament 211 at the intersection of edges 214 and 215. The relative motion of the inner member and outer member 213 causes the window 216 in the outer member to cease to coincide with the window 214 of the inner member. It should be noted that design of the edges 214 and 215 may be implemented in a variety of fashions. In FIGS. 27A and 27B, 214 is beveled and 215 is straight. Alternatively 215 may be beveled and 214 may be straight. In fact a successful scissors action may be achieved when windows 214 and 215 are both straight, particularly if the windows 214 and 216 are configured in such a way that the intersection of the edges 214 and 215 moves somewhat helically as outer member 213 is moved proximally.

Figure 28A:
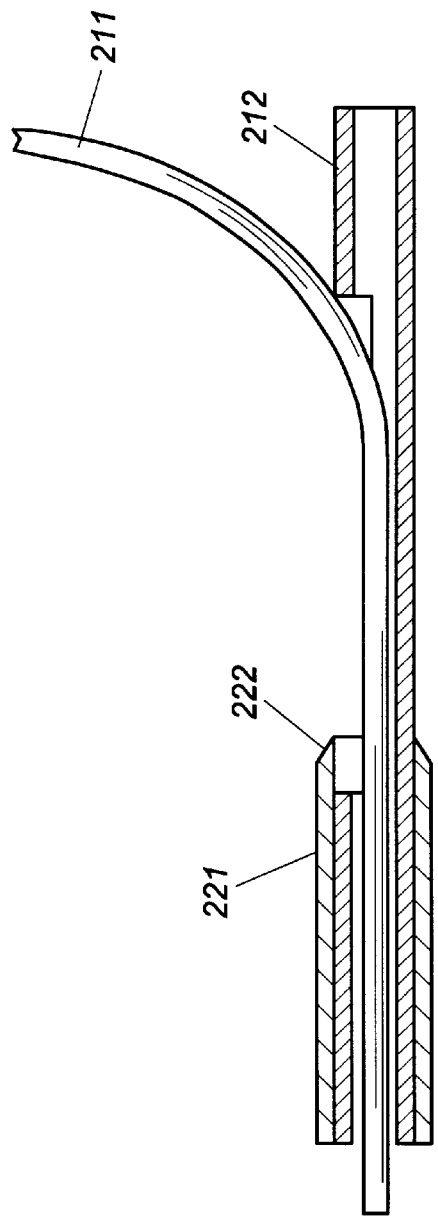
FIGS. 28A and 28B illustrate an embodiment wherein the outer member is pushed distally with respect to the inner member to achieve cutting.
Figure 28B:
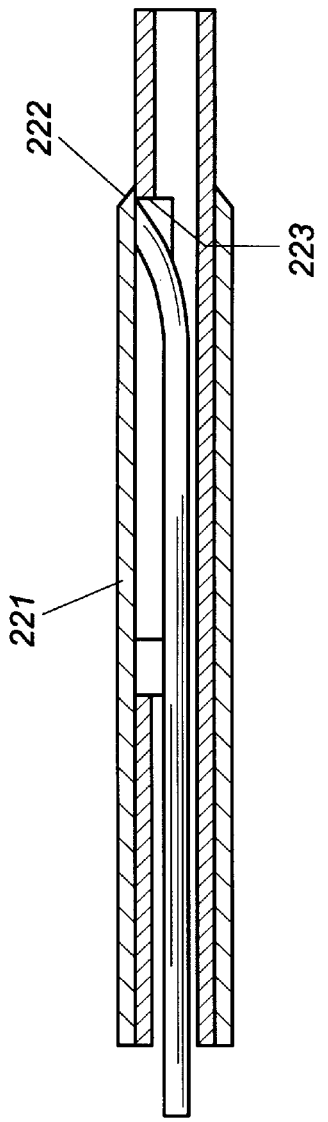

FIGS. 28A and 28B illustrate an embodiment wherein the outer member is pushed distally with respect to the inner member to achieve cutting. In this figure the design is similar to that shown in FIGS. 27A and 27B. Here pushing the outer member 221 distally causes passage of the beveled edge 222 of outer member 221 by the straight edge 223 of inner member 212 and consequent cutting of filament 211. Equivalently, edge 223 may be beveled and 222 may be straight, or both may be beveled, or neither may be beveled.

Figure 29A:
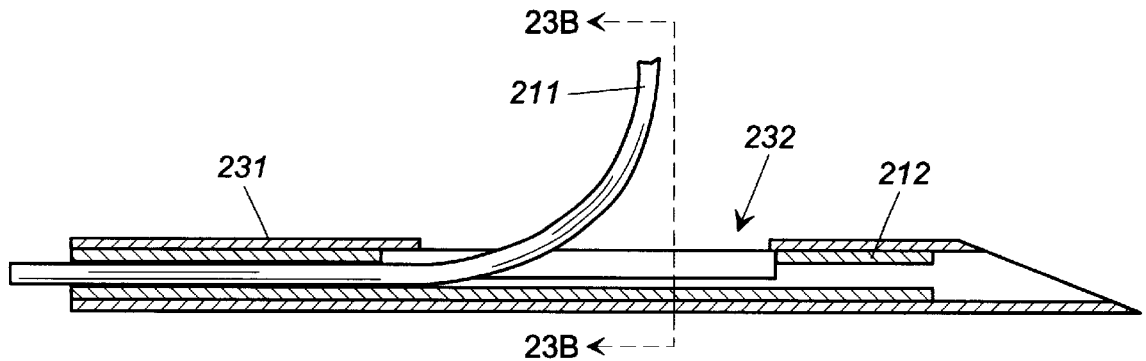
FIGS. 29A through 29C illustrate an embodiment wherein the inner and outer members are rotated with respect to one another to achieve cutting.
Figure 29B:
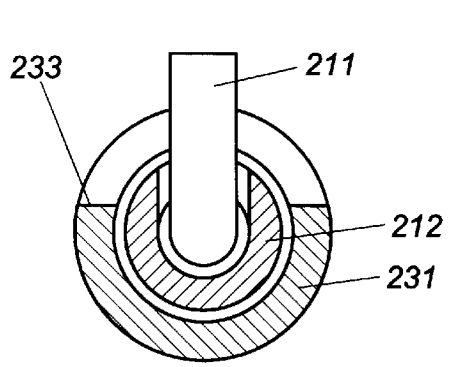
Figure 29C:
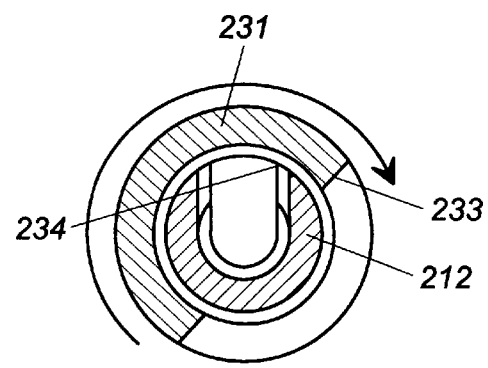

FIGS. 29A through 29C illustrate an embodiment wherein the inner and outer members are rotated with respect to one another to achieve cutting. The outer member 231 is permitted to rotate around inner member 212 to cause cutting of the fiber 211 emerging through the window 232. The effect of the rotation can be seen in the cross section taken at BB and shown in FIGS. 29B and 29C. The effect of the rotation is to cause edge 233 of outer member 231 to slice the filament 211 against the edge 234 of inner member 212.

Figure 30A:
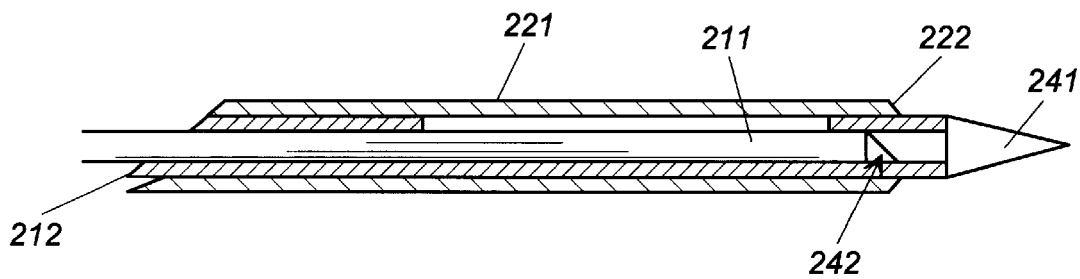
FIGS. 30A through 30D illustrate the way a tip, having a cutting arrangement of one of the types described above, may be employed in conjunction with a suitable window to prevent the presentation of undue pressure, by the distal end of the filament, on tissue of the subject on whom the invention may be used.
Figure 30B:
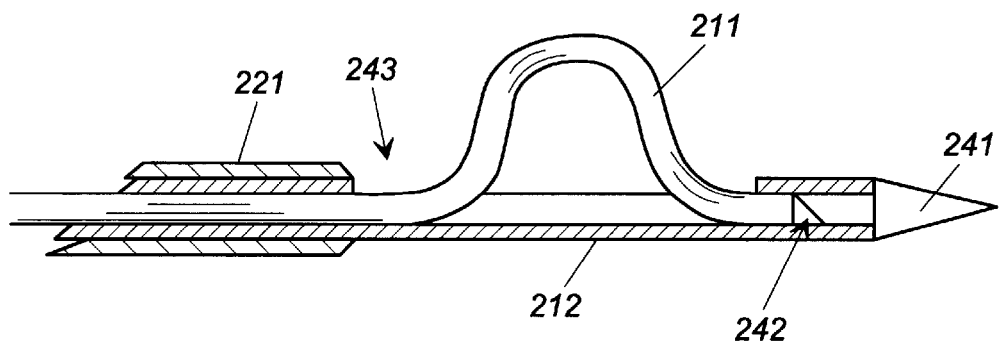
Figure 30C:
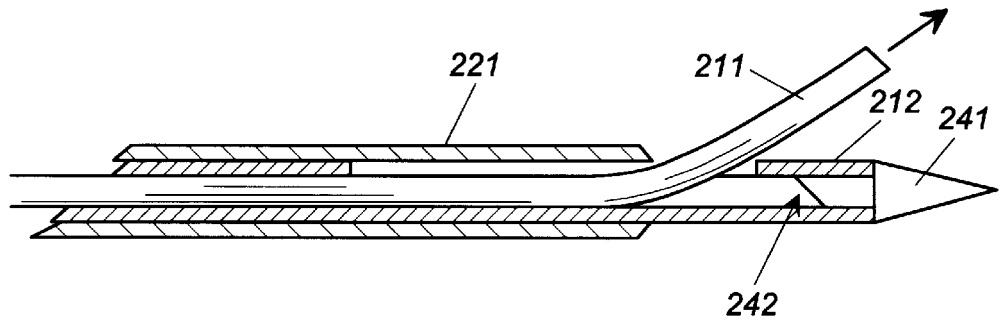
Figure 30D:
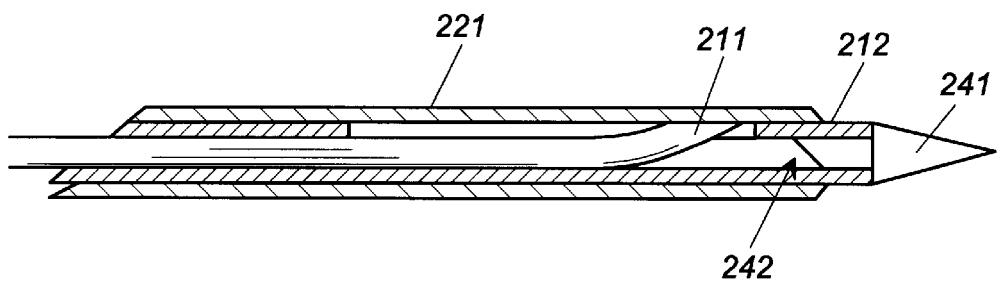

FIGS. 30A through 30D illustrate the way a tip, having a cutting arrangement of one of the types described above, may be employed in conjunction with a suitable window to prevent the presentation of undue pressure, by the distal end of the filament, on tissue of the subject on whom the invention may be used. In FIGS. 30A through 30D is shown a push cutter arrangement similar to that shown and discussed in connection with FIGS. 28A and 28B. There is thus an outer member 221 having a bevel 222 and an inner member 212. A window 243 is provided in the inner member to permit the emergence of a loop of filament 211. The end of the filament may be suitably captured in region 242 near the tip 241 of inner member 212. Using a filament-advance engine in accordance with a suitable embodiment such as described above, the filament may be caused to leave the exit window 243 while keeping the end of the filament engaged near the tip 241. The advantage of following such a procedure is that the loop of filament material will exert less pressure on tissue than would a free end; in this way the risk of lesion to surrounding tissue is reduced. In the course of advancing the filament into tissue, the end of the filament will eventually leave the tip region 242; however at this point, owing to the presence of a substantial portion of filament length already present, the forces associated with movement at the end of the filament are dramatically reduced. After a desired quantity of filament has been implanted, the outer member 221 is used to cause cutting of the filament 211. Cutting is initiated therefore by moving outer member 221 distally, as shown in FIG. 30C. In FIG. 30D, the filament 211 has been cut, and it can be seen that by further advancing the filament. The end will again be engaged in tip region 242, so that when desired the window 243 can again be opened by withdrawal of the outer member 221 and the process begun anew.

It will be appreciated that the size of the exit window 243 may be selected to take into account the particular nature of the implantation desired and the filament employed. For example, if it is desired that the material be concentrated in a very small region or if the filament is very flexible, then a smaller exit window may be appropriate, whereas if a larger region is to be treated or a stiffer filament is used, a larger exit window will be indicated.

In general, when a guide wire is utilized in connection with a cannula used for filament implantation herein, the guide wire may be utilized in a separate lumen of the cannula. Alternatively, it is within the scope of the present invention to utilize a common lumen for both the guide wire and the filament.

FIGS. 31A and 31B, and 32A and 32B, illustrate a possible configuration for a case for an embodiment similar to that of FIGS. 26A and 26B. In this configuration a cannula for insertion of the filament may be attached at fitting 251, and a handle 253 for actuating a cutter is also provided. A cable assembly 254 is removably attachable to the body of 255 to supply rotational power to the tool. Knob 252 is coupled to an internally located spool of filament.

The described embodiments of the inventions are intended to be merely exemplary and numerous variations and modifications will be apparent to those skilled in the art. All such variations and modifications are intended to be within the scope of the present invention as defined in the appended claims.

What is claimed is:

1. A device for inserting a filament having a diameter into a site in the body of a subject, the device comprising:
   a. an outer cannula having an axis, an interior wall, a distal end for inserting into the site, and a proximal end;
   b. an inner cannula having an inner diameter corresponding generally to the diameter of the filament, said inner cannula being disposed in coaxial telescoping relation with respect to said outer cannula;
   c. a mounting arrangement permitting axial movement of the inner cannula with respect to said outer cannula;
   d. an actuator mechanism for urging the inner cannula in axial reciprocation consisting of forward motion and retrograde motion with respect to the mounting arrangement; and
   e. coupling means for releasably coupling to said inner cannula a portion of a filament contained within said inner cannula to cause said filament to move with said inner cannula during forward motion of said inner cannula with respect to said mounting arrangement and for releasing said filament during retrograde motion of said inner cannula to permit said inner cannula to reciprocate rearward without causing said filament to move with said inner cannula.

2. A device according to claim 1, wherein the inner diameter of the inner cannula is approximately equal to the diameter of the filament.

3. A device according to claim 1, wherein the actuator mechanism further comprises a gripper for grasping the filament synchronously with forward motion of the inner cannula.

4. A device according to claim 1, wherein the feeding mechanism further comprises a second gripper acting out of phase with the first gripper for retaining the filament during retrograde motion of the inner cannula.

5. A device according to claim 1, wherein the feeding mechanism further comprises a brake for retaining the filament during retrograde motion of the inner cannula.

6. A device according to claim 1, wherein the inner cannula comprises distinct distal and proximal segments.

7. A device according to claim 1, further comprising a containment spring for retracting the distal segment of the inner cannula toward the proximal segment of the inner cannula during retrograde motion of the distal segment of the inner cannula.

8. The device of claim 1, wherein said inner cannula comprises a cutout window in a side wall thereof, and wherein said coupling means comprises an actuating pad which clamps said filament through said cutout window in a direction transverse to the longitudinal axis of said inner cannula.

9. The device of claim 8, wherein said actuator mechanism comprises a mechanism for moving said actuating pad in a direction parallel to said longitudinal axis of said inner cannula, whereby said actuating pad both clamps said filament and urges the inner cannula in axial reciprocation.

10. A device for inserting a filament having a diameter into a site in the body of a subject, the device comprising:
  a. an outer cannula having an axis, an interior wall, a distal end for inserting into the site, and a proximal end;
  b. an inner cannula having an inner diameter corresponding generally to the diameter of the filament, said inner cannula being disposed in coaxial telescoping relation with respect to said outer cannula;
  c. a mounting arrangement permitting axial movement of the inner cannula with respect to said outer cannula;
  f. an actuator mechanism for urging the inner cannula in axial reciprocation consisting of forward motion and rearward motion with respect to the mounting arrangement; and
  g. brake means for releasably holding a portion of the filament stationary with respect to said mounting arrangement to permit said inner cannula to reciprocate rearward without causing said filament to move with said inner cannula.

11. A device according to claim 10, wherein the inner diameter of the inner cannula is approximately equal to the diameter of the filament.

12. The device of claim 10, wherein said inner cannula comprises a cutout window in a side wall thereof, and wherein said device further comprises an actuating pad which clamps said filament through said cutout window in a direction transverse to the longitudinal axis of said inner cannula.

13. The device of claim 12, wherein said device further comprises a mechanism for moving said actuating pad in a direction parallel to said longitudinal axis of said inner cannula, whereby said actuating pad both clamps said filament and urges the inner cannula in axial reciprocation.

* * * * *